(12) United States Patent
Sweeney

(10) Patent No.: US 7,608,062 B2
(45) Date of Patent: Oct. 27, 2009

(54) METHOD AND DEVICE FOR DELIVERING MEDICINE TO BONE

(75) Inventor: Patrick J. Sweeney, Flossmoor, IL (US)

(73) Assignee: Spinal Generations, LLC, Olympia Fields, IL (US)

( * ) Notice: Subject to any disclaimer, the term of this patent is extended or adjusted under 35 U.S.C. 154(b) by 576 days.

(21) Appl. No.: 10/682,307

(22) Filed: Oct. 9, 2003

(65) Prior Publication Data

US 2005/0015060 A1      Jan. 20, 2005

Related U.S. Application Data

(63) Continuation-in-part of application No. 10/620,287, filed on Jul. 15, 2003.

(51) Int. Cl.
*A61M 5/00* (2006.01)
(52) U.S. Cl. .......................... 604/264; 606/62
(58) Field of Classification Search ............ 604/264; 606/72, 73, 80, 93, 60
See application file for complete search history.

(56) References Cited

U.S. PATENT DOCUMENTS

| | | | |
|---|---|---|---|
| 4,399,814 A | 8/1983 | Pratt, Jr. et al. | |
| 4,653,489 A | 3/1987 | Tronzo | |
| 4,760,844 A | 8/1988 | Kyle | |
| 4,976,692 A | 12/1990 | Atad | |
| 5,047,030 A | 9/1991 | Draenert | |
| 5,203,770 A * | 4/1993 | Wigness et al. | 604/506 |
| 5,425,723 A | 6/1995 | Wang | |
| 5,618,286 A | 4/1997 | Brinker | |
| 5,681,289 A * | 10/1997 | Wilcox et al. | 604/175 |
| 5,702,372 A | 12/1997 | Nelson | |
| 5,800,407 A | 9/1998 | Eldor | |
| 5,871,484 A * | 2/1999 | Spievack et al. | 606/60 |
| 6,019,761 A * | 2/2000 | Gustilo | 606/62 |
| 6,048,343 A * | 4/2000 | Mathis et al. | 606/72 |
| 6,077,265 A | 6/2000 | Werding et al. | |
| 6,210,376 B1 * | 4/2001 | Grayson | 604/264 |
| 6,214,012 B1 | 4/2001 | Karpman et al. | |
| 6,220,888 B1 | 4/2001 | Correa | |
| 6,228,088 B1 | 5/2001 | Miller et al. | |
| 6,387,098 B1 * | 5/2002 | Cole et al. | 606/62 |

(Continued)

FOREIGN PATENT DOCUMENTS

WO    WO 02/098307    12/2002

OTHER PUBLICATIONS

Final Office Action for U.S. Appl. No. 10/620,287, mailing date Jul. 23, 2008, 9 pages.

(Continued)

*Primary Examiner*—Nicholas D Lucchesi
*Assistant Examiner*—Laura A Bouchelle
(74) *Attorney, Agent, or Firm*—Foley & Lardner LLP

(57) ABSTRACT

Fenestrated bone screws and inserts disposed therein are provided for the delivery of medicants to bone. The bone screws provide a method to strengthen or repair damaged bones, or to promote bony fusion, and in conjunction with the inserts, provide a method of delivering a continuous or regulated amount of medicant to a desired location within the bone such as a fracture interface. In one embodiment, the inserts are customized in size, shape, or configuration after the bone screw has been inserted into the patient.

11 Claims, 25 Drawing Sheets

U.S. PATENT DOCUMENTS

| | | | |
|---|---|---|---|
| 6,679,890 | B2 | 1/2004 | Margulies et al. |
| 2001/0021852 | A1 | 9/2001 | Chappius |
| 2002/0138146 | A1 | 9/2002 | Jackson |
| 2003/0045885 | A1 | 3/2003 | Margulies et al. |
| 2003/0212426 | A1 | 11/2003 | Olson, Jr. et al. |
| 2004/0225292 | A1 | 11/2004 | Sasso et al. |
| 2006/0111767 | A1 | 5/2006 | Olson et al. |

OTHER PUBLICATIONS

Non-Final Office Action for U.S. Appl. No. 10/704,526, mailing date Sep. 15, 2008, 10 pages.

Cecil, M. L. et al., "Projection of the S2 Pedicle Onto the Posterolateral Surface of the Ilium—A Technique for Lag Screw Fixation of Sacral Fractures or Sacroiliac Joint Dislocations," Spine 1996, vol. 21, pp. 875-878; www.kalindra.com/project.htm.

Sato, T. et al., "Calcium Phosphate Augmentation of Screw Fixation in Femoral Neck Fracture," 47$^{th}$ Annual Meeting, Orthopaedic Research Society, Feb. 25-28, 2001, San Francisco, California.

Press release from Spine Center Atlanta, "New Screw Debut Firsttime Use for New Spinal Surgery Device," 2002, Orthopaedic & Spine Surgery of Atlanta LLC; www.SpineCenterAtlanta.com.

Final Office Action for U.S. Appl. No. 10/620,287, mailing date of Jul. 27, 2007, 9 pages.

Interview Summary for U.S. Appl. No. 10/620,287, mailing date of Oct. 5, 2007, 3 pages.

\* cited by examiner

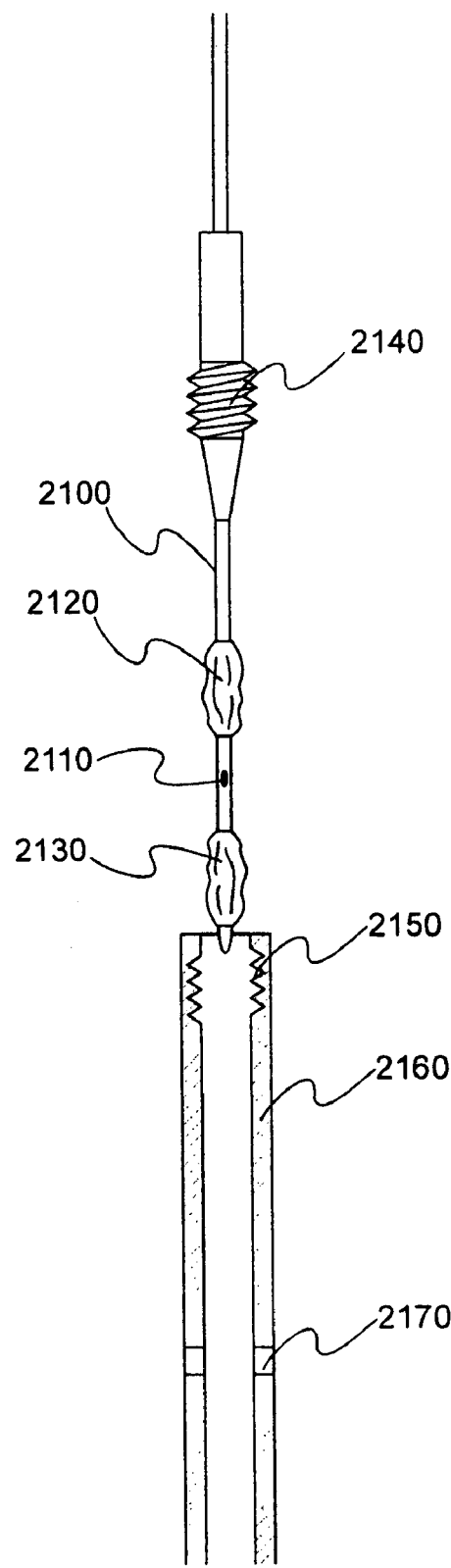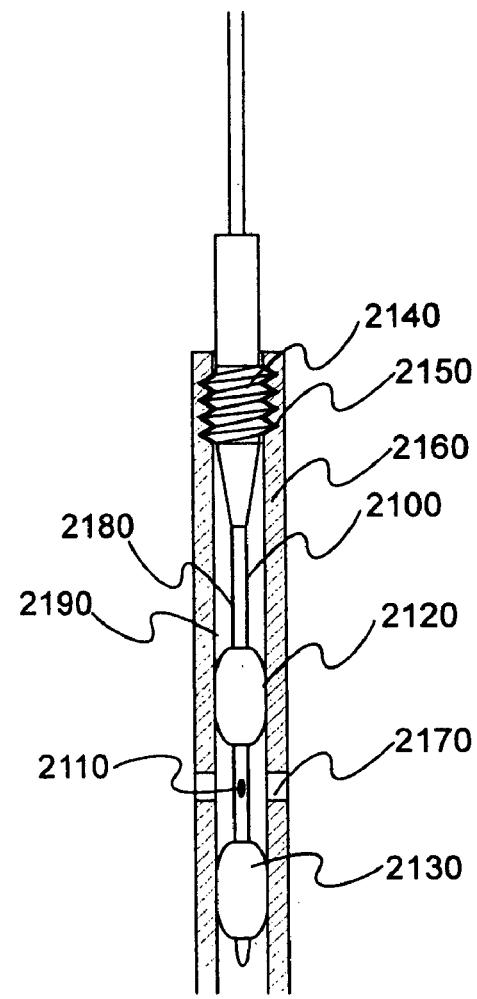
Fig. 21
Fig. 22

METHOD AND DEVICE FOR DELIVERING MEDICINE TO BONE

CROSS-REFERENCES TO RELATED APPLICATIONS

This application claims priority as a continuation-in-part application of U.S. patent application Ser. No. 10/620,287, filed Jul. 15, 2003, the entire disclosure of which is incorporated herein by reference and for all purposes.

FIELD OF THE INVENTION

The present invention relates to devices and methods for delivering substances such as medicants to bones. More particularly, the present invention concerns devices and methods for delivering substances to the interior or exterior of fractured or otherwise injured bones, especially to the fracture interface thereof. The devices may also be used to promote fusion of a joint.

BACKGROUND OF THE INVENTION

Delivery of medicants or therapeutics to bones is an often desirable but difficult-to-achieve process, especially if one desires to focus the delivery to the interior of a bone or to a particular area in a bone. Delivery pins or needles, such as those disclosed in U.S. Pat. No. 6,210,376, the disclosure of which is hereby incorporated by reference herein, are sometimes used to deliver medication or other fluids into bone. Such pins are typically made of metals such as titanium or steel, and must be fabricated ahead of time for later use. Thus, it is difficult to customize the pins for directing the delivery of medicants or fluids to a specific area of interest within a bone. Moreover, such pins do not serve as fixation screws for holding two or more bones or bone pieces in a fixed spatial relationship with respect to each other.

Bone screws can be used to repair or strengthen fractured or otherwise damaged or diseased bones, often by fixing two or more bones or bone pieces with respect to each other, in which case the bone screw may be referred to as a fixation screw. Such screws have been adapted to deliver liquids such as bone cements to the interior of a bone, and are disclosed in U.S. Pat. Nos. 5,047,030 and 6,214,012, for example, the disclosures of which are hereby incorporated by reference herein. These devices must be fabricated ahead of time for later use, thereby substantially limiting the ability to customize the device to the needs of an individual patient. Moreover, while these devices may be suitable for the one-time delivery of a curable substance such as a bone cement, they provide no way to control or regulate the amount of substance delivered. Substance delivery also cannot be directed to certain areas within the bone and not others without changing the location or configuration of the bone screw itself.

Thus, a need exists for a device capable of delivering a substance to a bone, especially to specific areas within the bone, such as a fracture interface. In addition, a further need exists for the ability to customize the delivery location and amount during the course of an operation, once the bone screw is in place, for example.

SUMMARY OF THE INVENTION

In accordance with the present invention, a bone-screw insert is disposed within a bone screw to provide a device for the delivery of a desired substance to the interior or exterior of a bone or its surrounding tissues. The bone screws and the inserts are cannulated along at least a portion of their lengths. The bone screws are fenestrated and the inserts are either fenestrated or permeable to the substance to be delivered such that when the insert is disposed within the bone screw a delivery pathway exists whereby the substance can be delivered from one end of the insert to the exterior of the bone screw through the bone-screw fenestrations.

In one aspect of the present invention the bone screw comprises a fixation screw whereby two or more bones or bone pieces may be held in a fixed spatial relationship with respect to each other. It may often be desirable to deliver a substance at or near the fracture interface of a broken bone, for example. In such a case, the desired positions of bone-screw fenestrations which will align with or match this location may not be known until after the bone screw has been disposed within the bone. The bone-screw inserts of the present invention thus allow one to selectively block the bone-screw fenestrations to which substance delivery is not desired, while maintaining a substance delivery pathway to one or more bone-screw fenestrations to which substance delivery is desired.

In another aspect of the invention, the device comprises a reservoir which may serve as a source of the one or more substances to be delivered to the vicinity of a bone. Reservoirs useful in the practice of this invention may comprise the cannulated portions of the bone screw or insert, or they may be reservoirs that are connected to the bone screw or insert for substance delivery. In certain embodiments the present invention may further comprise a pump for facilitating the delivery of the one or more substances to the vicinity of a bone. Such pumps may, for example, aid in the continuous or regulated flow of a fluid into the bone screw or insert for delivery to the desired location.

Yet another aspect of the invention provides a method for administering a substance to a bone. The method comprises introducing a cannulated, fenestrated bone screw into a bone, introducing a cannulated insert into the bone screw, and introducing a substance to be delivered into the cannulated portion of the insert. The method may further comprise the use of a fenestrated or permeable insert, or the use of reservoirs or pumps to aid in substance delivery. In certain embodiments of the invention the insert may initially serve the purpose of preventing bone fragments, blood, fat, or other materials from entering the cannulated portion of the bone screw, especially during insertion of the bone screw into the bone, for example. This may then be followed by readjustment or realignment of the insert to provide a pathway for the substance to be delivered at a later point in time.

BRIEF DESCRIPTION OF THE DRAWINGS

FIG. 21 shows an insert having deflated balloons along its length being inserted into a bone screw.

FIG. 22 shows the insert of FIG. 21 with inflated balloons disposed inside the bone screw.

DETAILED DESCRIPTION OF THE PREFERRED EMBODIMENTS

Figure 1:
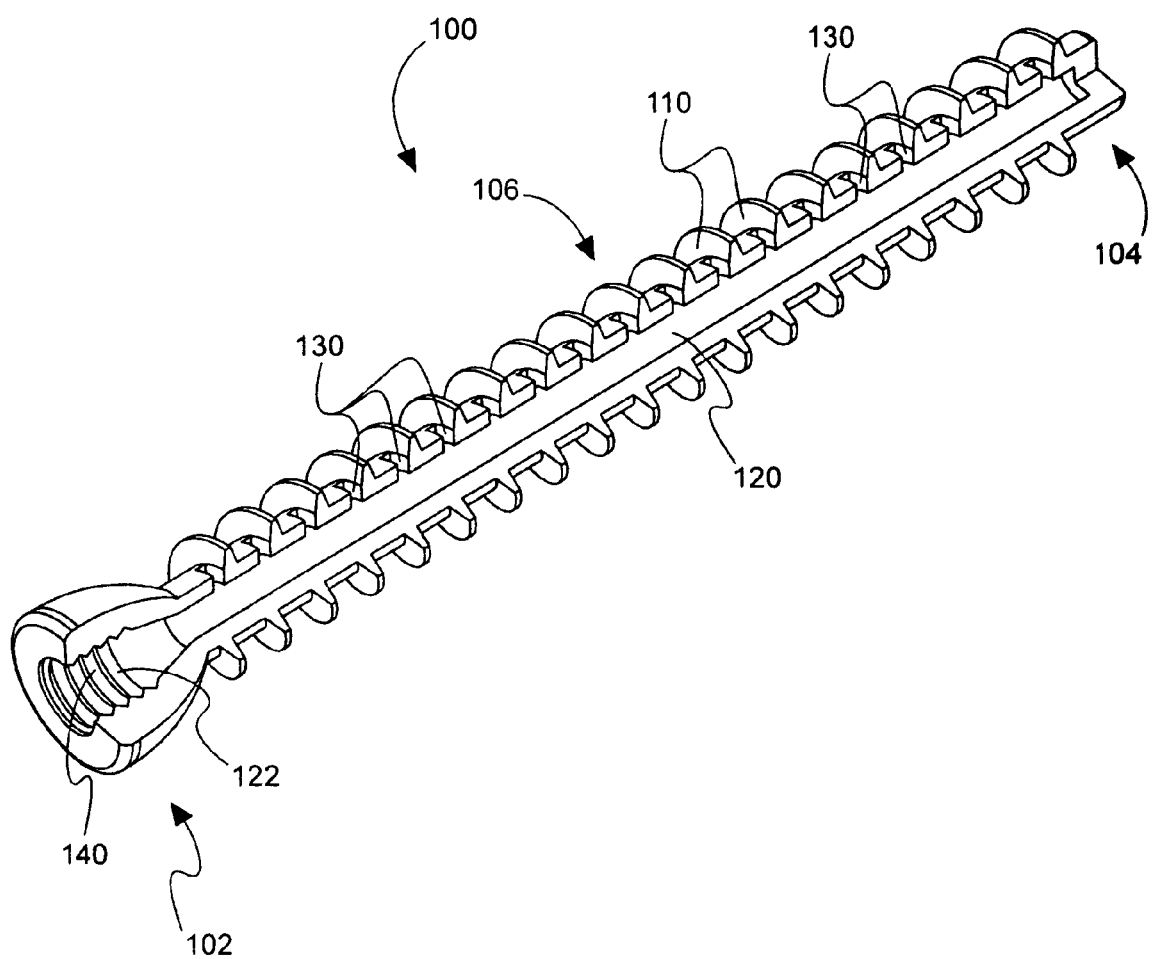
FIG. 1 shows a perspective view of a bone screw in accordance with the present invention.

In accordance with the present invention, a bone-screw-insert is disposed within a fenestrated bone screw, and the combination is used to deliver desired substances to the vicinity of a bone. The bone screw and the insert are cannulated along at least a portion of their lengths. In certain embodiments, the insert may also be fenestrated. The inserts of the present invention may be comprised of a single piece, or alternatively the insert may be comprised of several pieces or sections. In certain embodiments, the bone screw may be a fixation screw used to hold two or more bones or bone pieces in a fixed spatial relationship with respect to each other. The substances to be delivered may comprise medicants or therapeutics, or other substances which are desirable to deliver to the vicinity of a bone. The substance or a combination of substances may be delivered to the interior of the bone, to the exterior of a bone, to the fracture interface between two or more broken bones, or to any other location which may be facilitated by utilization of the present invention.

For the purposes of this invention, the term "cannulated" means that the screw or insert comprises a hollow cavity disposed inside at least part of its shaft. For example, the cavity may consist of a bore beginning at or near one end of the screw or insert and extending longitudinally into the screw or insert. Other configurations are possible, however, and the hollow cavity need not be restricted to a cylindrical shape or a circular cross-section. The cavity may extend throughout the entire length of the screw or insert, thus creating openings at each end of the screw or insert, or alternatively, the cavity may extend only partially into the interior of the screw or insert. The shape and size of the cavity may be suitably chosen to allow delivery of the desired substance through the screw or insert to the bone area of interest. When it is desired to use the cannulated portion of the screw or insert as reservoir for the substance to be delivered, for example, the cavity may be made as large as possible so long as the screw and insert maintain the structural integrity needed for introduction into the bone.

For the purposes of this invention, the term "fenestration" is used broadly to include any slot, gap, or perforation that defines an opening between the inside of the cannulated portion of the screw or insert to the outside of the screw or insert whereby a desired substance may be delivered. Thus, a fenestrated screw comprises an opening which defines a substance delivery pathway between the internal cannulated portion and the exterior of the screw. Likewise, a fenestrated insert is one that comprises an opening which defines a substance delivery pathway between the internal cannulated portion and the exterior of the insert. In certain embodiments of the present invention where a fenestrated insert is utilized in combination with a fenestrated screw, at least one screw fenestration and at least one insert fenestration may be designed to align with each other once the screw and insert are in their appropriate configuration and position. Alignment or coordination of an insert fenestration and a screw fenestration will define a substance delivery pathway between the internal cannulated portion of the insert and the exterior of the screw.

In accordance with the present invention, fenestrations will typically extend in the radial direction from the internal cannulation to the exterior of the screw or insert, but other configurations are possible. Such fenestrations are separate and distinct from the opening at or near the one end of the screw or insert created by the cannulation. Further in accordance with the present invention, the fenestrations may be any desired shape or size desired to effect the delivery of the desired substance. For example, the fenestration cross-sections may be round, oval, or square. The fenestration cross-sections may, if desired, change shape between the inside and the outside of the screw or insert. Any number or combination of fenestrations may be located along the shaft or at the ends of the screws and inserts of the present invention. The insert fenestrations may be larger or smaller than the screw fenestrations.

An insert may have an outside diameter large enough such that the outside of the insert is pressed snuggly against the inside of the cannulation when the insert is in a bone screw in order to prevent the substance to be delivered from leaking between the insert and the bone screw and escaping through a bone screw fenestration from which it was not intended to escape. Alternatively, the insert may include one or more balloons along its length. These balloons, each of which is disposed around a portion of the insert, may be deflated when the insert is placed into the bone screw and subsequently inflated. Upon inflation, each balloon forms a seal between the outside of the insert and the inside of the bone screw. Using this construction, one or more insert fenestrations and one or more bone screw fenestrations may be isolated between two inflated balloons, such that a substance delivered through the isolated insert fenestrations may exit only through bone screw fenestrations positioned between the inflated balloons. Inserts having different lengths and/or different balloon placements may be provided such that the appropriate insert and bone screw fenestrations may be isolated to provide an appropriate delivery pathway depending on the final position of the bone screw in a patient relative to the desired delivery location.

For the purposes of this invention, the term "bone screw" is intended to refer to screws of all types which are presently known or hereafter devised for implantation into bone. In this regard, cancellous screws, cortical screws, and machine screws are all contemplated as being within the scope of the types of screws useful in the practice of the present invention. The bone screws of the present invention will typically comprise threads along at least a portion of the exterior of the screw shaft, but it should be appreciated that tacks, pins, nails and the like may also be included within the definition of a bone screw for the purposes of the present invention, whether threaded or unthreaded. When threads are present, it may be found advantageous to use self-tapping threads, or alternatively, the threads can be pre-cut in the bone prior to bone-screw insertion.

Referring now to FIG. 1, there is disclosed a bone screw 100 having two ends 102 and 104 connected by a shaft 106, and bone screw threads 110. The cut-out of FIG. 1 reveals that bone screw 100 comprises a cannulated portion 120, and bone screw fenestrations 130 along the length of the cannulated portion 120. It will be appreciated by one skilled in the art that the fenestrations 130 need not be even spaced along the cannulated portion 120, but may be arranged in a desired pattern or frequency along the length of the cannulated portion 120. It will be further appreciated by one skilled in the art that one end 122 of the cannulated portion 120 of the bone screw 100 is configured to accept a bone screw insert. For example, the bone screw 100 may comprise additional threads 140 on the one end 122 of the cannulated portion 120 to promote fixation of a bone screw insert.

In one embodiment of the current invention the bone screw may be a fixation screw used to hold two or more bones or bone pieces in a fixed spatial relationship with respect to each other. Fixation screws are known in the art. One such device is disclosed by Tronzo, U.S. Pat. No. 4,653,489, the disclosure of which is hereby incorporated by reference herein. In accordance with the present invention, the bone screw may be used to mend peripheral skeletal fractures or osteotomies, repair a spondyloysis or an odontoid fracture, or fuse lumbar facet joints, for example. Other beneficial uses of bone screws, and more particularly, fixation screws, will be known to one skilled in the art and are to be included within the scope of the present invention.

Figure 2:
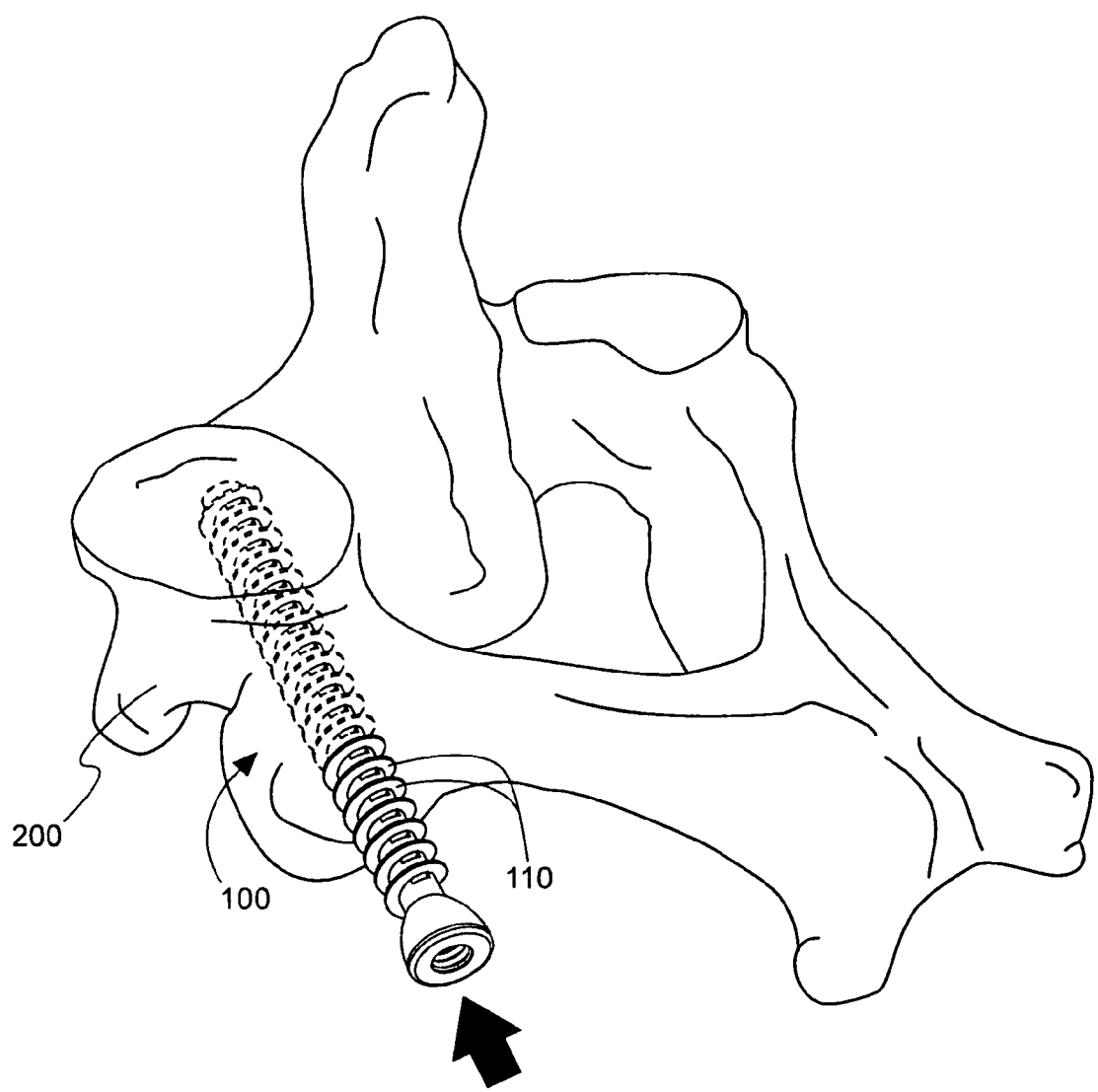
FIG. 2 shows a bone screw inserted into the hip bone of a patient.

Referring now to FIG. 2, there is disclosed a bone screw 100 disposed partially within a bone 200. Bone 200 may, for example, represent a human hip bone. In one embodiment, bone screw 100 is disposed within bone 200 by rotating the bone screw 100 such that the bone screw threads 110 act to pull bone screw 100 into bone 200, thereby anchoring bone screw 100 into place.

Bone screws of the present invention may comprise any material suitable for placement into a bone without harmful effects on the patient. Examples of suitable materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalciumphosphate. Other materials useful for bone screw construction will be known to those skilled in the art, and are to be included within the scope of the present invention.

Figure 3A:
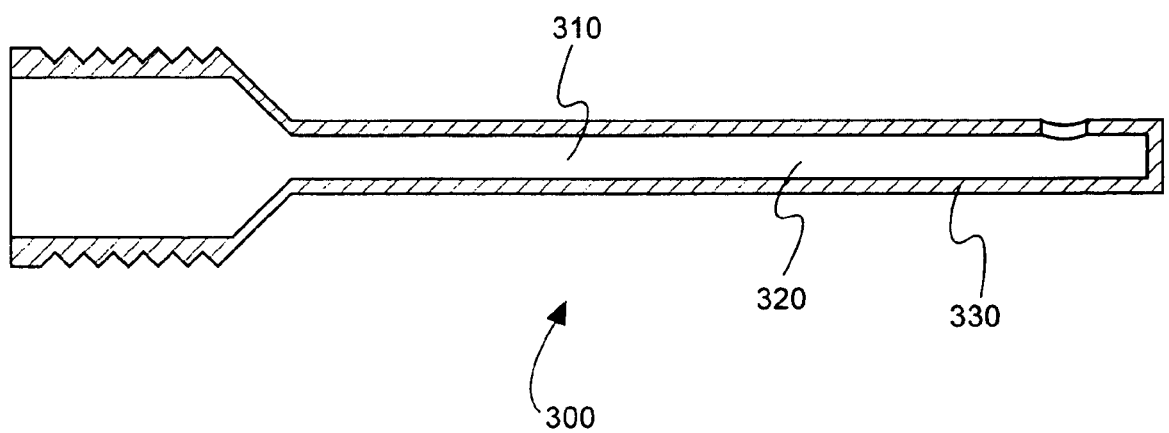
FIG. 3(a) shows a schematic cross-sectional view of a bone-screw insert with a single fenestration.
Figure 3B:
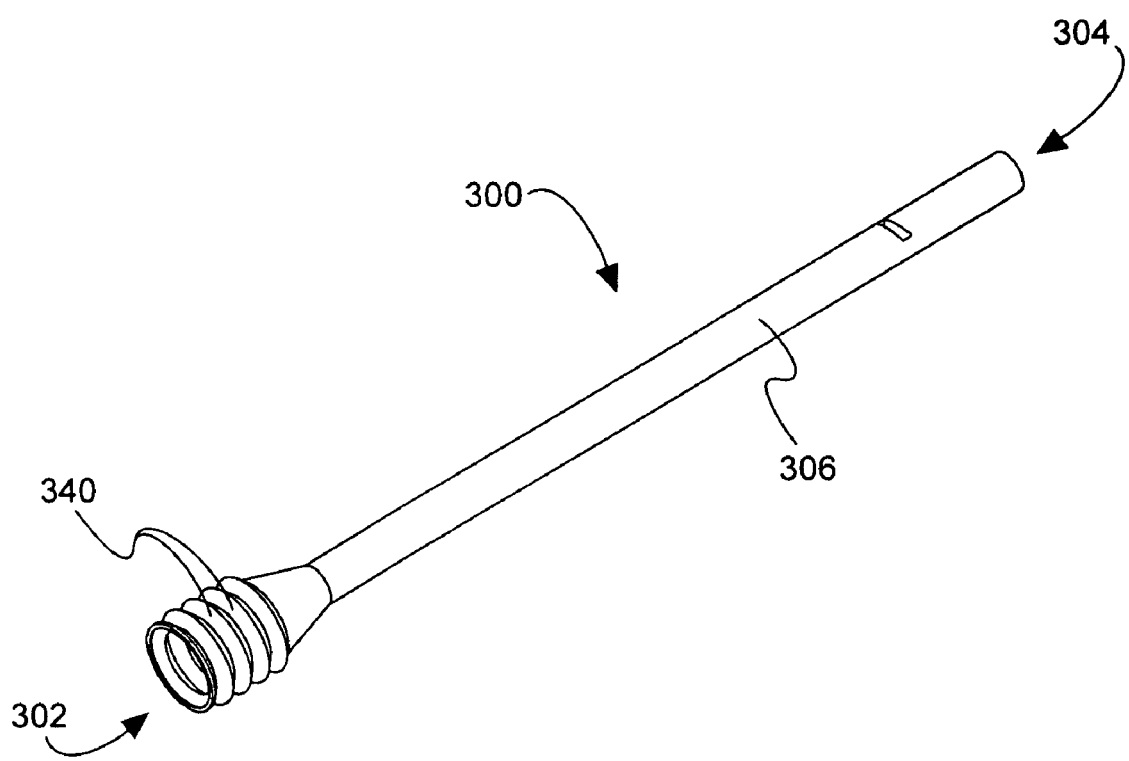
FIG. 3(b) shows a perspective view of the bone-screw insert of FIG. 3(a).

The device of the present invention further comprises a bone-screw insert. For the purposes of this invention, the term "insert" is used to refer to one or more cannulated members which are disposed within the cannulated portion of a bone screw. Referring now to FIG. 3(a), the insert 300 comprises a cannulated portion 310 which consists of a hollow cavity 320 surrounded by the insert wall 330, where the cavity and wall dimensions may be suitably chosen in order to carry out the practice of the invention disclosed herewith. In certain embodiments, the insert may comprise a single piece, as disclosed in FIG. 3(a). Alternatively, the insert may comprise two or more pieces or sections that, when taken together, form the insert of the present invention. Referring now to FIG. 3(b), when the insert 300 is a single piece, the insert comprises two ends, 302 and 304, connected by a shaft 306. The shaft may be cannulated along its entire length, creating openings at each end of the insert. Alternatively, the cannulation may extend only partially into the shaft so long as the cannulation is sufficient to allow for delivery of a substance from one end of the insert to one or more bone-screw fenestrations. One end 302 of the insert 300 may comprise threads 340 which interlock with bone screw threads 140 of FIG. 1 to help fix an insert 300 into a bone screw 100. When the insert comprises two or more pieces or sections, only one of the sections need be cannulated such that the insert sections, when taken together, allow for delivery of a substance from one end of the insert to one or more bone-screw fenestrations.

Figure 4:
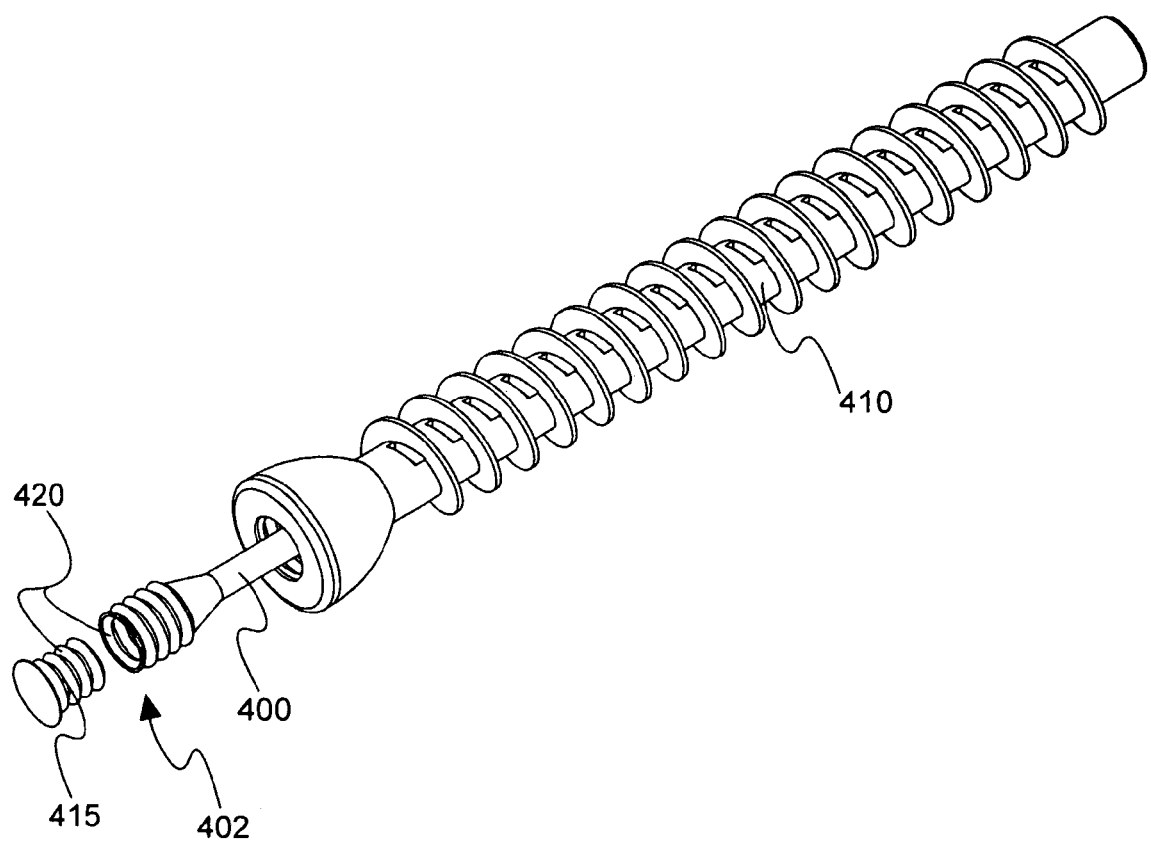
FIG. 4 shows a perspective view of a bone screw, a bone-screw insert, and an insert cap, in accordance with the present invention.

In one embodiment of the present invention, the exterior dimensions of the insert are only slightly smaller than the interior dimensions of a cannulated bone screw to provide for a tight but sliding fit when the insert is placed into the bone screw, as depicted in FIG. 4 in which an insert 400 is shown partially disposed within a bone screw 410. Also disclosed in FIG. 4 is an insert cap 415 which can be used to substantially seal the one end 402 of the insert 400 via insert cap threads 420 either before, during, or after the bone screw 410 and insert 400 are put into place. The insert may have substantially the same cross-sectional shape as the cannulated portion of the bone screw, or their cross-sectional shapes may be different. For example, the internal bone screw cavity and the exterior surface of the insert may have a substantially circular cross-section. One advantage of this embodiment is that after the insert has been disposed within the bone screw, the insert may be rotated with respect to the screw to achieve alignment of certain of the insert and bone-screw fenestrations, for example. In another embodiment, the insert and bone screw may have substantially non-circular cross-sections such that the insert is not free to rotate once it has been disposed within the bone screw. In yet another embodiment, at least part of the insert cross-section may not match that of the bone screw cavity such that when the insert is disposed within the bone screw, one or more channels are formed longitudinally along at least part of the insert and bone screw shafts. Such channels may be useful, for example, to allow air or fluids to escape the bone screw cavity as the insert is introduced.

Figure 5A:
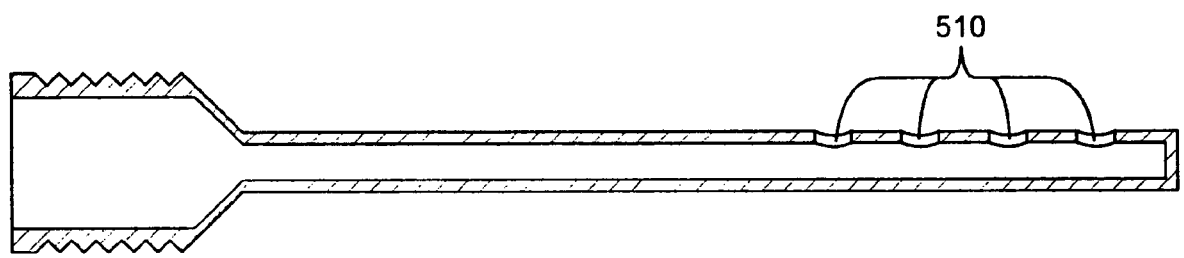
FIG. 5(a) shows a schematic cross-sectional view of a bone-screw insert with multiple fenestrations.
Figure 5B:
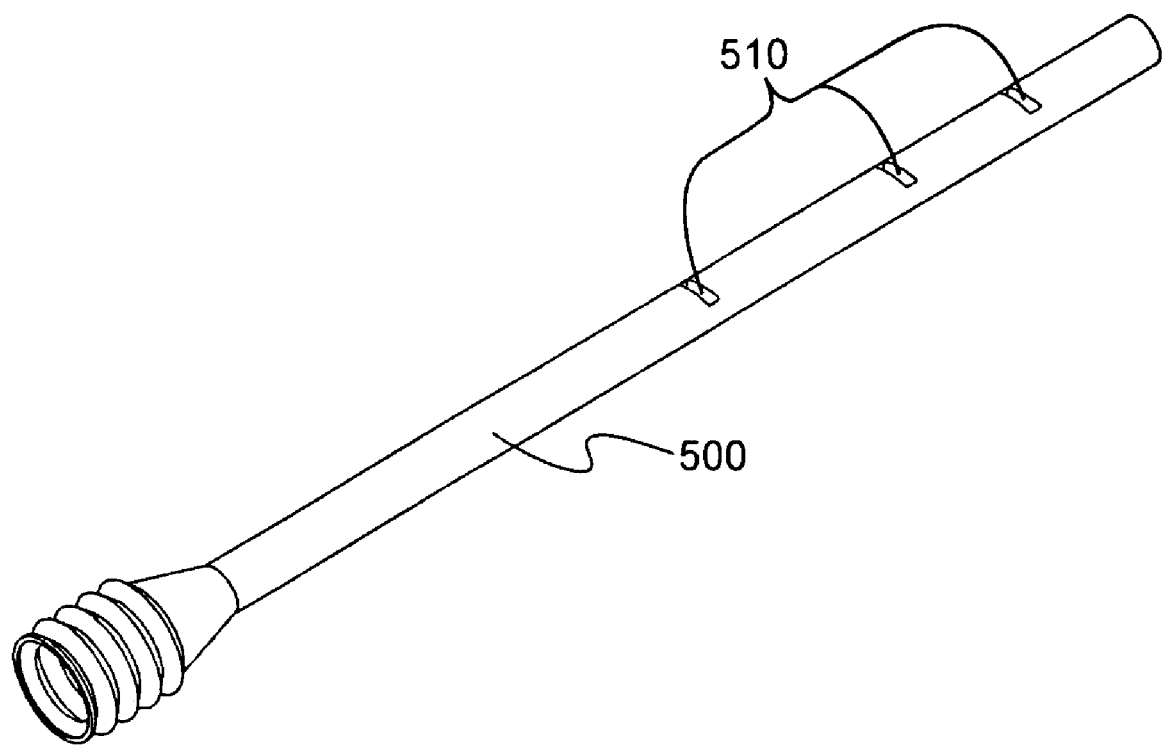
FIG. 5(b) shows a perspective view of the bone-screw insert of FIG. 5(a).

When substantially unimpeded delivery of a substance to one or more bone-screw fenestrations is desired, the inserts of the present invention may comprise one or more insert fenestrations 510, as depicted in FIG. 5(a). An insert having an appropriate number, size, shape, and location of insert fenestrations can be chosen by the practitioner without undue experimentation to provide a delivery pathway between at least one end of the insert and the one or more bone-screw fenestrations. For example, FIG. 5(b) discloses an insert 500 comprising a plurality of insert fenestrations 510 having a substantially rectangular cross-section. Alternatively, the delivery pathway may initiate at one end of the bone screw and pass through the insert to one or more bone-screw fenestrations. The insert fenestrations need not match the bone-screw fenestrations in number, size, shape, or location, although it may be advantageous to locate at least one of the insert fenestrations such that it may be substantially aligned with at least one bone-screw fenestrations once both the bone screw and the insert are in place.

Figure 6:
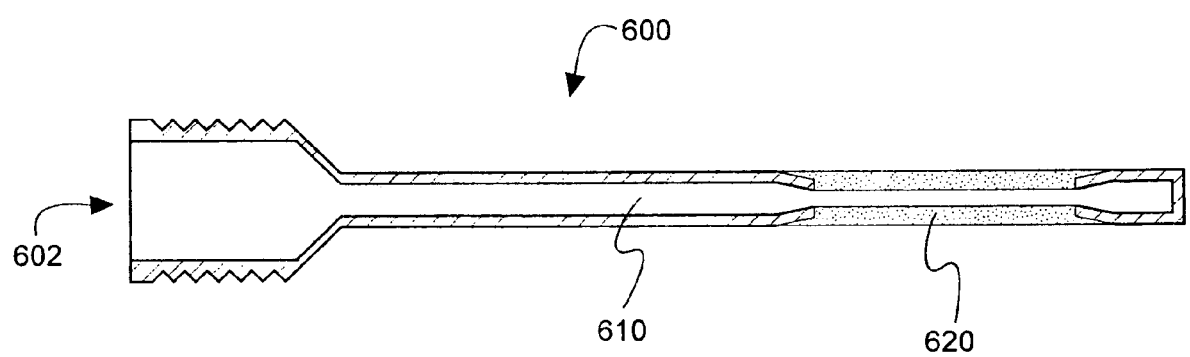
FIG. 6 shows a schematic cross-sectional view of a bone-screw insert with a porous section along the length of the shaft.

In another embodiment of the present invention, the inserts of the present invention may be permeable to the substance to be delivered such that the substance is delivered to the exterior of the insert by diffusion through the insert wall or through small openings in the insert wall. Such openings may be intentionally created such as by increasing the porosity of the insert material (e.g., by introducing a series of pinpricks into the material), or they may exist naturally as pores in the material. Referring to FIG. 6, there is disclosed an insert 600 comprising a cannulated portion 610 and a permeable material 620 wherein a substance to be delivered can travel from one end 602 of the insert to the permeable material 620. When the insert comprises a material that is at least partially permeable to the substance to be delivered, the insert may or may not be fenestrated so long as delivery of the desired substance is not completely impeded by the insert. An embodiment of the present invention comprising a permeable but non-fenestrated insert may be preferred when it is desired to effect a controlled, slow release of the desired substance to a bone, or when it is desired to prevent bone fragments, blood, fat or other materials or fluids from traveling from the exterior of the insert to the interior cavity.

Figure 7:
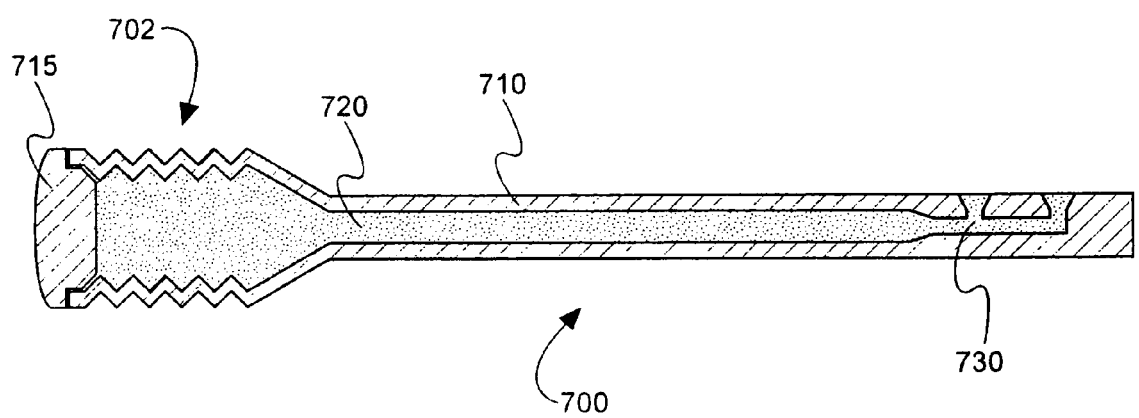
FIG. 7 shows a schematic cross-sectional view of a bone-screw insert with an internal reservoir and a cap.

When it is desired to use the cannulated portion of the insert as a reservoir for the substance to be delivered, or when the substance is to be delivered to a bone by permeation through the insert walls, it may be desirable to make the insert walls as thin as possible. Referring now to FIG. 7, there is disclosed an insert 700 with walls 710 surrounding a reservoir 720. One end 702 of the insert may be substantially sealed by insert cap 715. For example, in one embodiment, the insert may comprise a thin-walled tube which increases the available volume for storage of the substance, and which also increases the diffusion of the substance through the insert wall. In another embodiment, the insert may comprise a film or coating on the interior surfaces of the bone-screw cavity. Inserts in accordance with this embodiment may be as thin as a few hundred nanometers or less, which again may be beneficial for increasing the reservoir size with the bone screw and insert cavity, and for increasing the diffusion of the substance through the insert wall.

In another aspect of the present invention, the delivery of a substance to a bone may alternately be controlled or directed by diminishing the cavity size within the insert so that the movement of the substance is restricted. In this embodiment, it may be desired that the insert cannulation or insert fenestrations be a few microns (e.g., 5 microns) or less in size. Referring again to FIG. 7, there is further disclosed a cannulated portion 730 of insert 700 which is diminished in size so as to restrict or limit the flow of a substance from the reservoir 720. The exact configuration and geometry of an insert providing the desired level of substance delivery can be determined by one skilled in the art without undue experimentation, and all such configurations are to be included within the scope of the present invention.

In yet another aspect of the present invention, the inserts may control or direct the delivery of a substance to a bone through a fenestrated bone screw by substantially blocking one or more of the bone-screw fenestrations. This approach may be advantageous when it is desired to deliver the substance to a specific location with respect to the bone screw's position within the bone. Since the exact bone-screw fenestrations which align with or match this location may not be known until after the bone screw has been disposed within the bone, the bone screw inserts of the present invention allow one to selectively block the bone-screw fenestrations to which substance delivery is not desired, while maintaining a substance delivery pathway to one or more bone-screw fenestrations to which substance delivery is desired. Moreover, by utilizing an insert whereby the insert fenestrations align with the bone-screw fenestrations to which substance delivery is desired, one may achieve substantially unimpeded delivery of the substance to the area of interest.

In addition, the bone-screw inserts of the present invention, even when fenestrated, may be advantageously used to significantly hinder bone fragments, blood, fat, or other materials from entering the cannulated portion of the bone screw, especially during insertion of the bone screw into the bone, for example. In this case it may be desirable to initially position the insert and bone screw such that the insert fenestrations do not align with the bone-screw fenestrations. The insert may then be subsequently re-positioned at a later time to align one or more of the insert fenestrations with the bone-screw fenestrations to facilitate substance delivery.

Inserts of the present invention may comprise any material compatible with the bone screw and able to be placed within the bone screw without producing adverse effects to the patient. Examples of suitable insert materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalcium-phosphate. Other materials useful for insert construction will be known to those skilled in the art, and are to be included within the scope of the present invention. When the insert comprises two or more sections, the sections need not comprise the same material. In addition, when it is desired that the insert be permeable to the substance to be delivered, one or more of the insert sections may comprise a material specifically chosen to impart the desired level of permeability to the insert.

The insert may be sold or otherwise provided in a kit containing two or more inserts having different fenestrations or permeability characteristics. The availability of such a kit has the advantage of allowing a practitioner to select an appropriate insert based on the particular needs of the patient.

In accordance with the present invention, the insert is disposed within the bone screw to provide for a directed or controlled delivery of a desired substance to a bone. For the purposes of this invention, the term "substance" is used to refer to one or more chemical compounds that are useful when delivered to the vicinity of a bone. Substances may be chosen to help treat diseased bone as well as fractured or otherwise injured bones. Alternatively, the substance may be delivered to otherwise healthy bone to help maintain overall bone health, for example. Representative example substances include medicants or therapeutics such as antibiotics, chemotherapeutics, angiogenic factors, bone morphogenic proteins, and bone growth factors. Other desirable substances may be known or hereinafter determined by one skilled in the art, which are to be included within the scope of this invention.

Figure 8A:
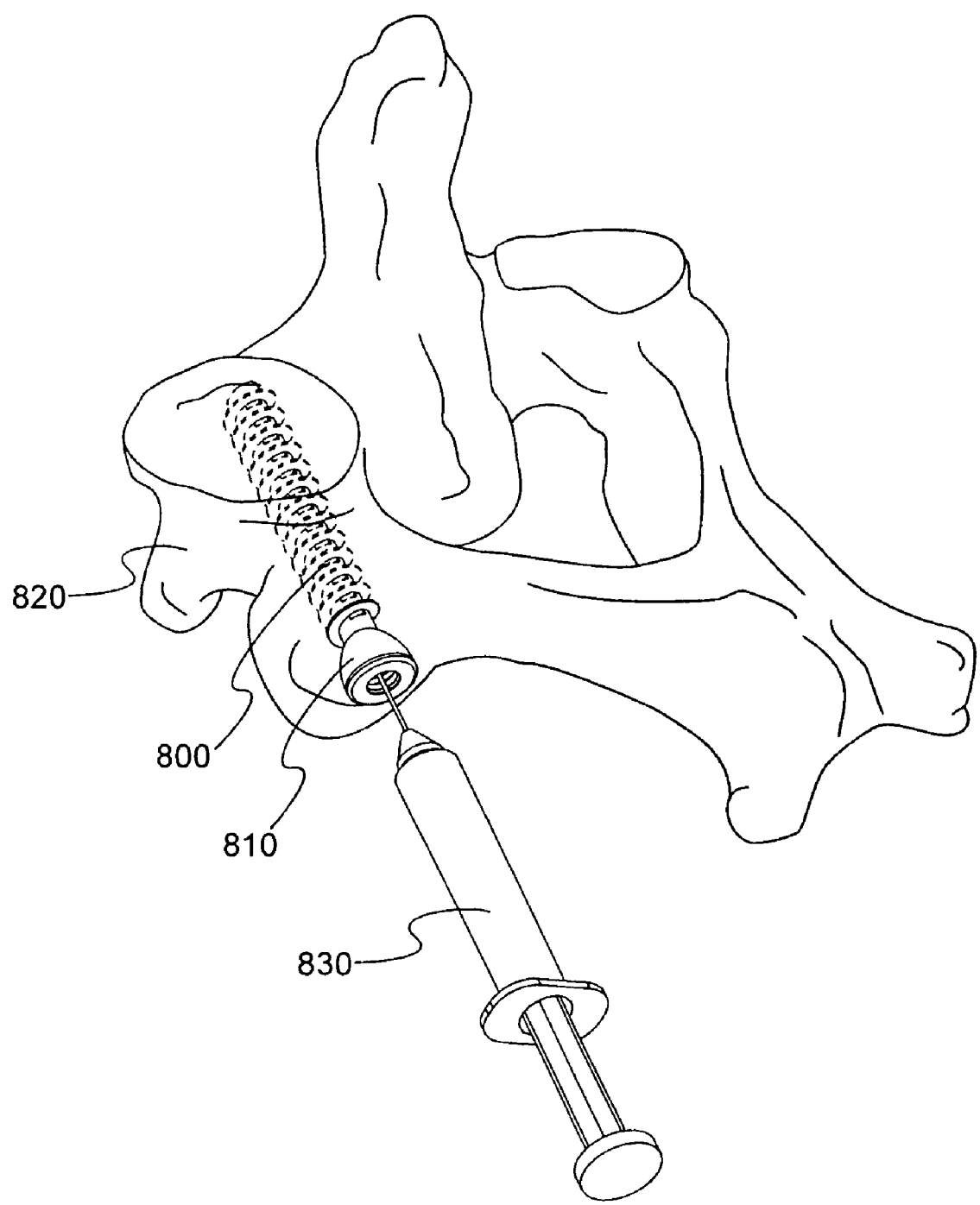
FIG. 8(a) shows a perspective view of a syringe being used to provide a liquid to a bone screw disposed in a hip bone.
Figure 8B:
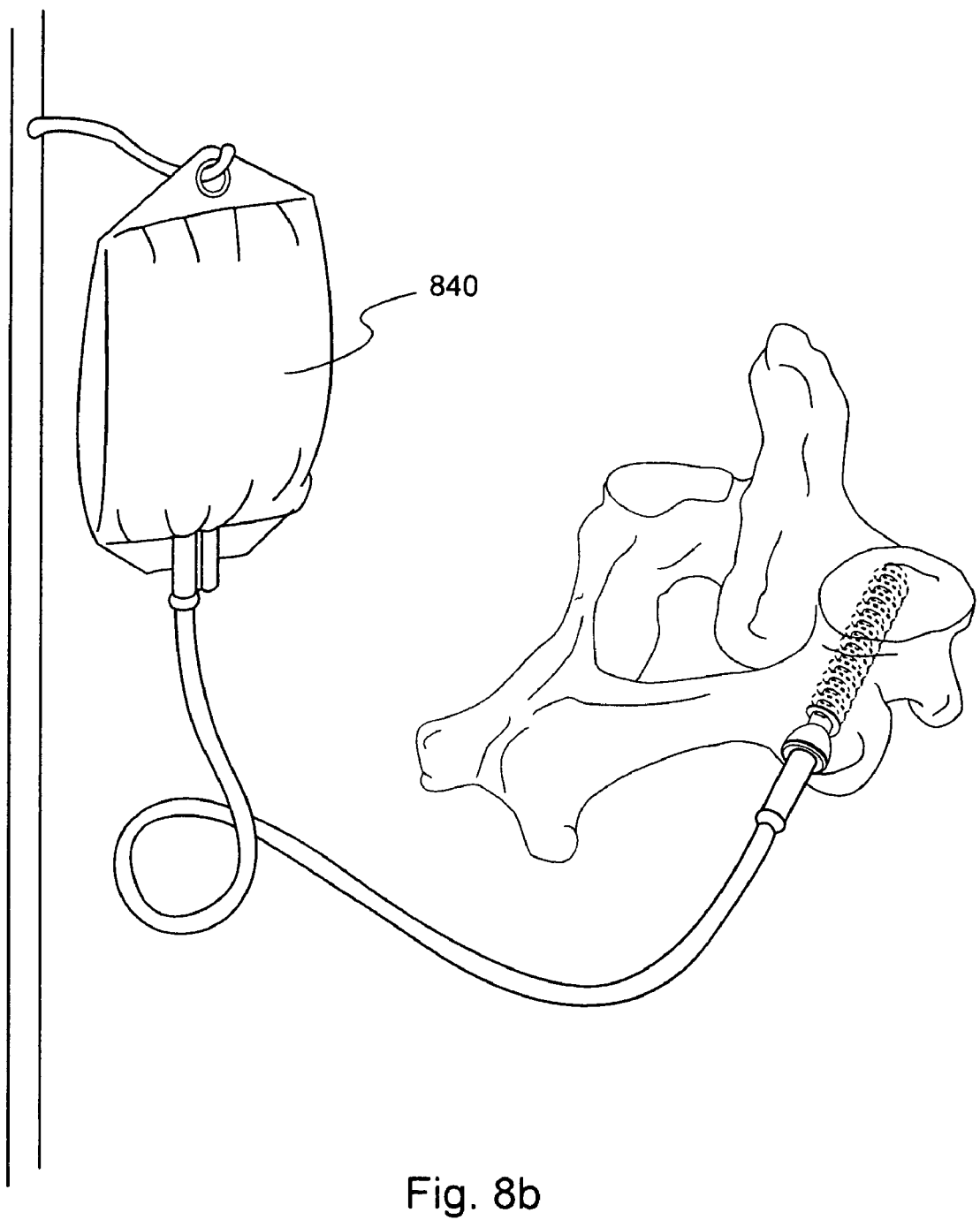
FIG. 8(b) shows a perspective view of a IV being used to provide a liquid to a bone screw disposed in a hip bone.

In certain applications of the present invention it may be desirable that the substance be stored in a reservoir prior to delivery to a bone. Thus, it may be advantageous for the device of the present invention to further comprise a reservoir. For the purposes of this invention, the term "reservoir" refers to any source of the one or more substances to be delivered to the vicinity of a bone. For example, the reservoir may comprise the hollow cavity created by the cannulation of the bone-screw insert and any part of the bone-screw cannulation not occupied by the insert, as depicted in FIG. 7 and described above. In one embodiment of the present invention, the substance to be delivered may be absorbed into a sponge-like material such as a collagen, for example, which may then be disposed within the cannulated portion of the bone screw or insert, or both. When additional reservoir space is desired, a suitable reservoir may be connected to the cannula opening of either the bone screw or insert. For example, FIG. 8(a) discloses a bone screw 800 and an insert 810 disposed therein, both of which are disposed within a bone 820. FIG. 8(a) further discloses a syringe 830 which acts as a reservoir in accordance with the present invention to provide a substance to the bone 820 via bone screw 800 and insert 810. Another embodiment of the present invention, is depicted in FIG. 8(b) which discloses an IV 840 which serves as a reservoir for delivering a substance to a bone via a bone screw and an insert. In yet another embodiment of the present invention, the reservoir may be implanted beneath the patient's skin, i.e., subcutaneously.

Figure 9:
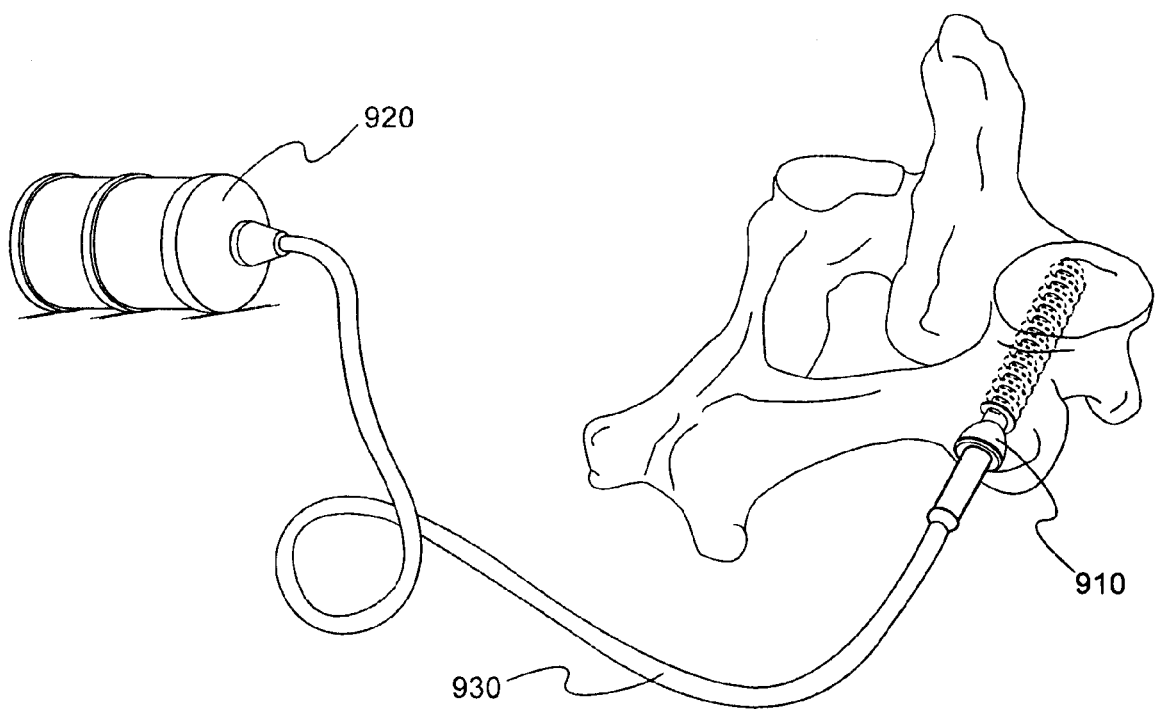
FIG. 9 shows a perspective view of a pump assembly being used to provide a liquid to a bone screw disposed in a hip bone.

In another aspect of the present invention, it may be advantageous for the device of the present invention to further include a pump 920, as depicted in FIG. 9, for delivering a substance to a bone via a bone screw and an insert 910, and tubing 930. A pump may be utilized to aid in delivery of the substance to the vicinity of a bone by, for example, delivering a continuous, regulated volume to the screw. The pump may also be used to increase the fluid pressure within the cannulated portion of the insert, thereby aiding fluid flow through the insert fenestrations or insert walls, for example. This embodiment may have the further advantage that the positive pressure created by the pump within the cannulated portion of the insert or bone screw hampers the influx of unwanted materials or compounds into the device. The pump may be connected to the cannulated portion of the bone screw or insert as depicted in FIG. 9, and the pump may also be implanted subcutaneously if desired. Examples of pumps which may be suitably used in the practice of the current invention are the implantable pumps disclosed in U.S. Pat. No. 4,588,394, for example. Other examples may be relatively simple pumps such as external pumps similar to those used with patient controlled anesthesia machines or simple IV pumps. These and other pump types and designs which may be currently known or hereinafter discerned by one skilled in the art are to be included within the scope of this invention.

In one embodiment of the invention the bone screw may be a fixation nail that holds two or more bones or bone parts in a fixed spatial relationship. In this embodiment the exterior of the bone screw shaft is unthreaded. In accordance with the invention, the fixation nail may be adapted for use in the fixation of a variety of bones, including, but not limited to, femur fixations, humerus fixations and tibia fixations.

Figure 10:
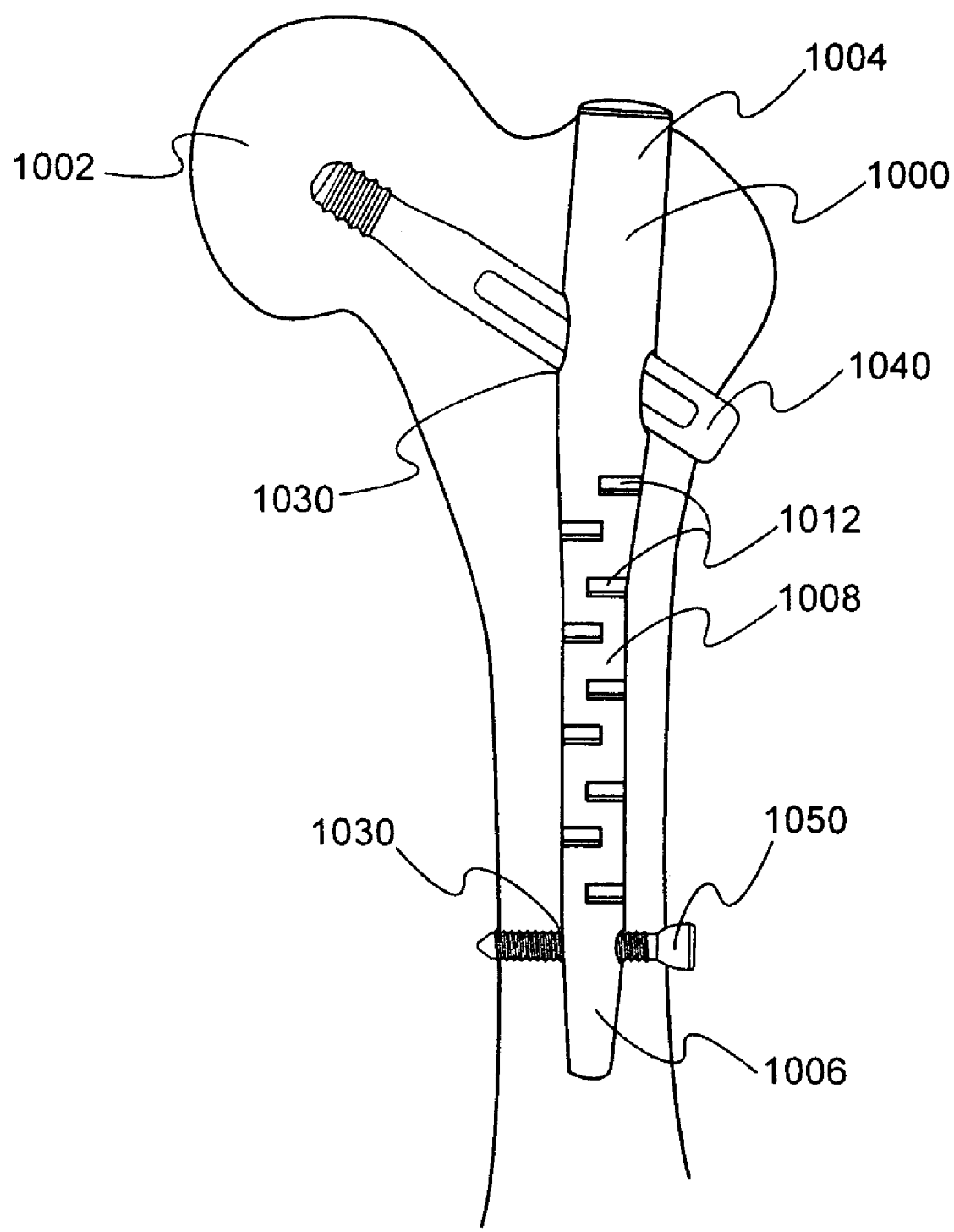
FIG. 10 shows a fixation nail inserted into the femur bone of a patient.
Figure 11:
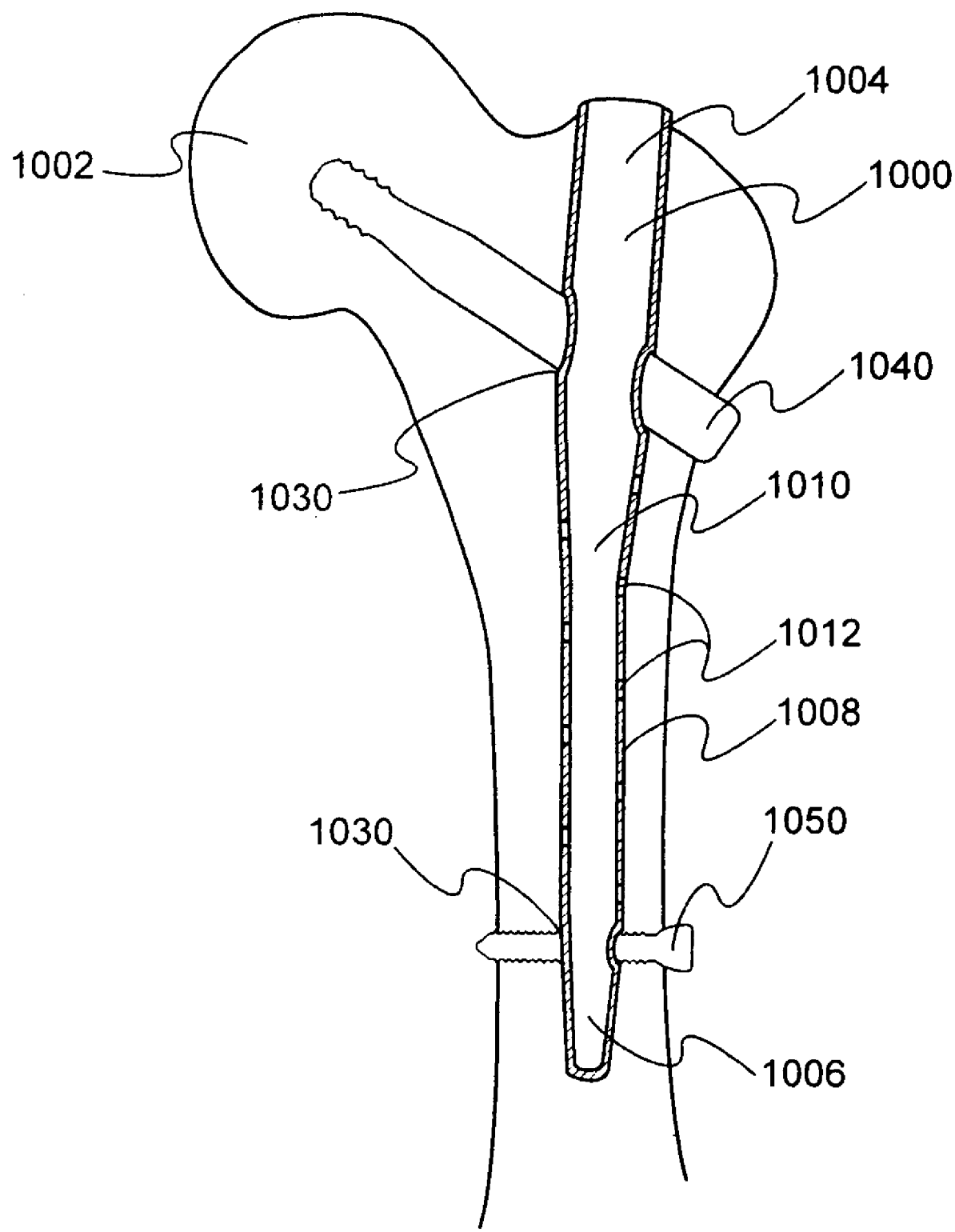
FIG. 11 shows a cross-sectional view of the fixation nail of FIG. 10.
Figure 12:
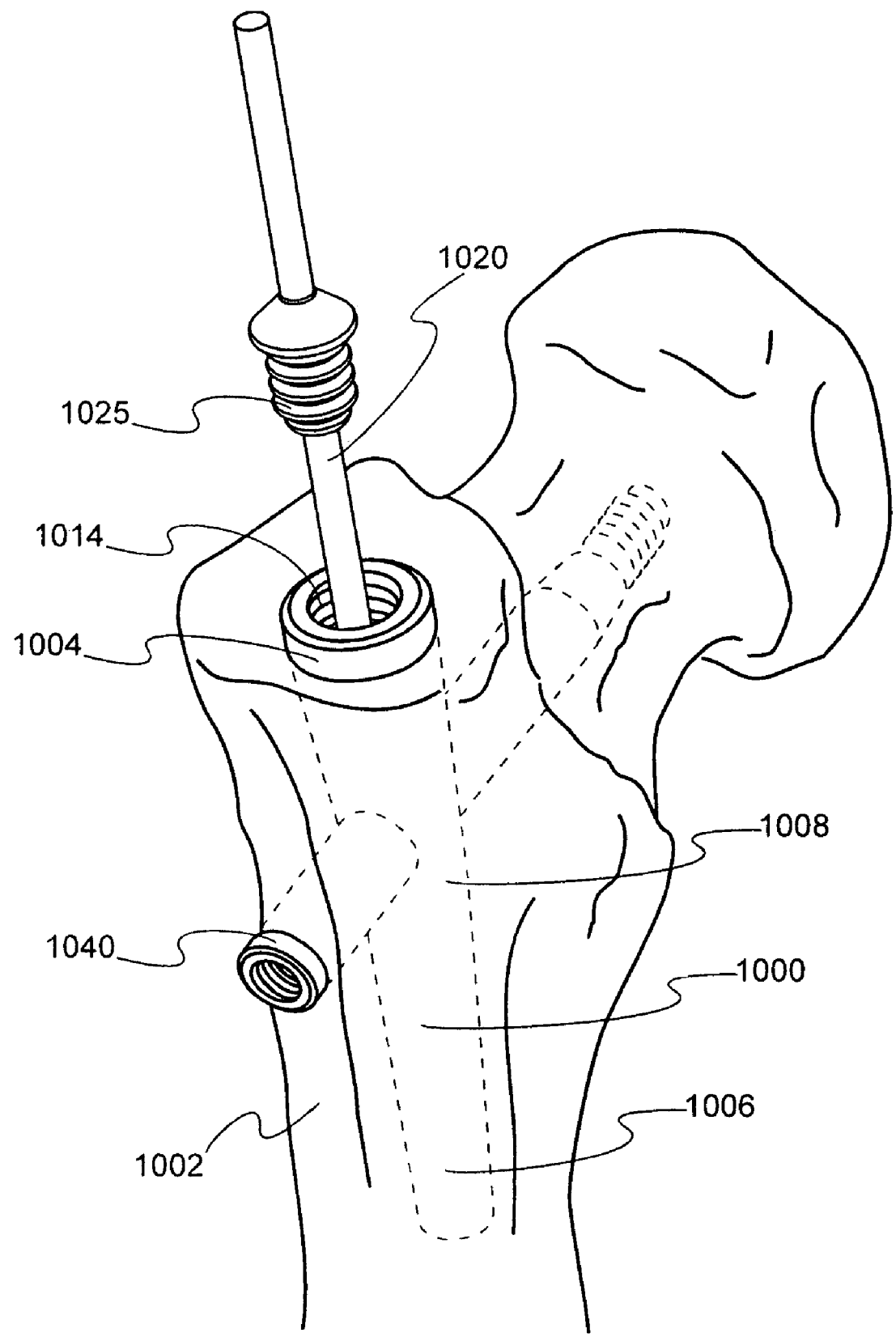
FIG. 12 shows a perspective view of a bone-screw insert being inserted into the fixation nail of FIG. 10.

Referring now to FIG. 10, there is disclosed a femur fixation nail 1000 disposed within a femur 1002. The fixation nail has two ends 1004 and 1006 connected by a shaft 1008. The fixation nail includes a cannulated portion 1010, which is best seen in the cross-sectional view of FIG. 11, and fixation nail fenestrations 1012 along the length of the cannulated portion 1010. One end of the cannulated portion 1010 of the fixation nail 1000 may be configured to accept a nail insert 1020. This is demonstrated in FIG. 12 which shows a perspective view of the fixation nail 1000 having internal threads 1014 on one end 1004 of the cannulated portion 1010 to promote fixation of a nail insert 1020 having threads 1025 on one end. As shown in the figures, the fixation nail may define one or more bores 1030 through its length through which fixation screws 1040 and 1050 may be passed in order to affix the fixation nail to the bone. The fixation screws may pass through the fixation nail substantially perpendicular to the long axis of the nail or they may pass through the nail at acute or obtuse angles with respect to the long axis of the nail. The dimensions of a fixation screw that passes through the cannulated portion of a fixation nail are desirably selected such that the screw does not substantially impede the passage of a substance to be delivered to the bone. In some instances, the fixation screw may itself include a bore through its length that allows for the passage of the substance.

Figure 13:
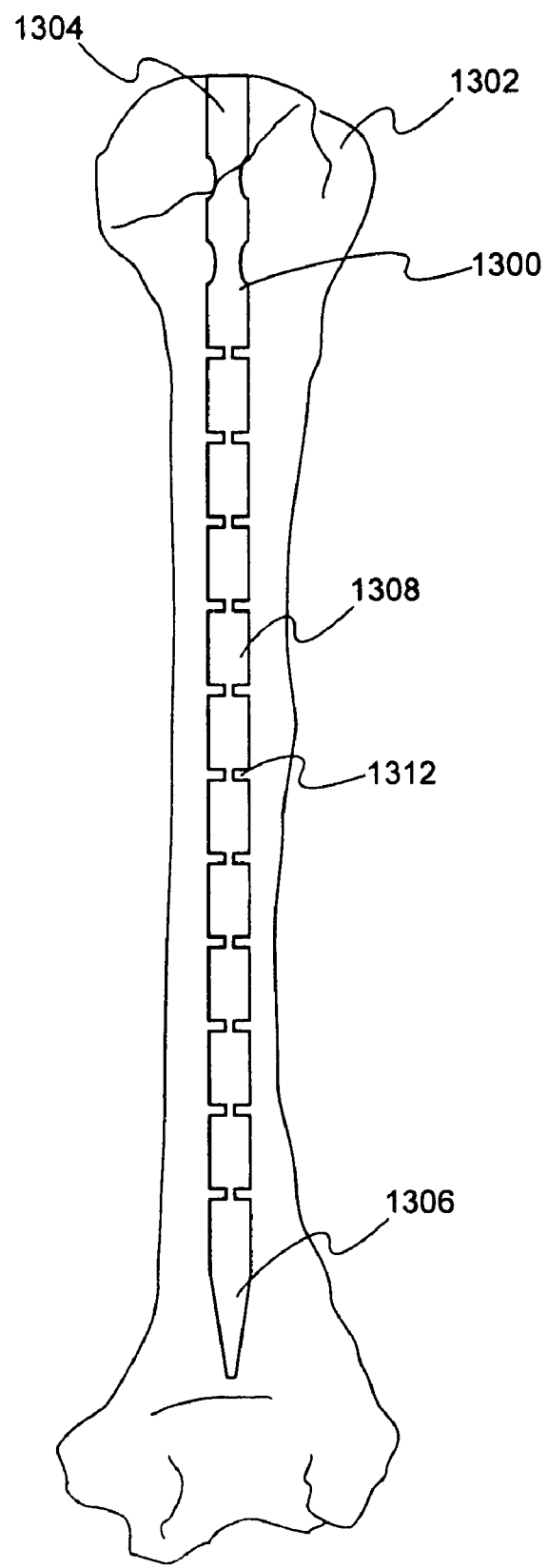
FIG. 13 shows a fixation nail inserted into the humerus bone of a patient.
Figure 14:
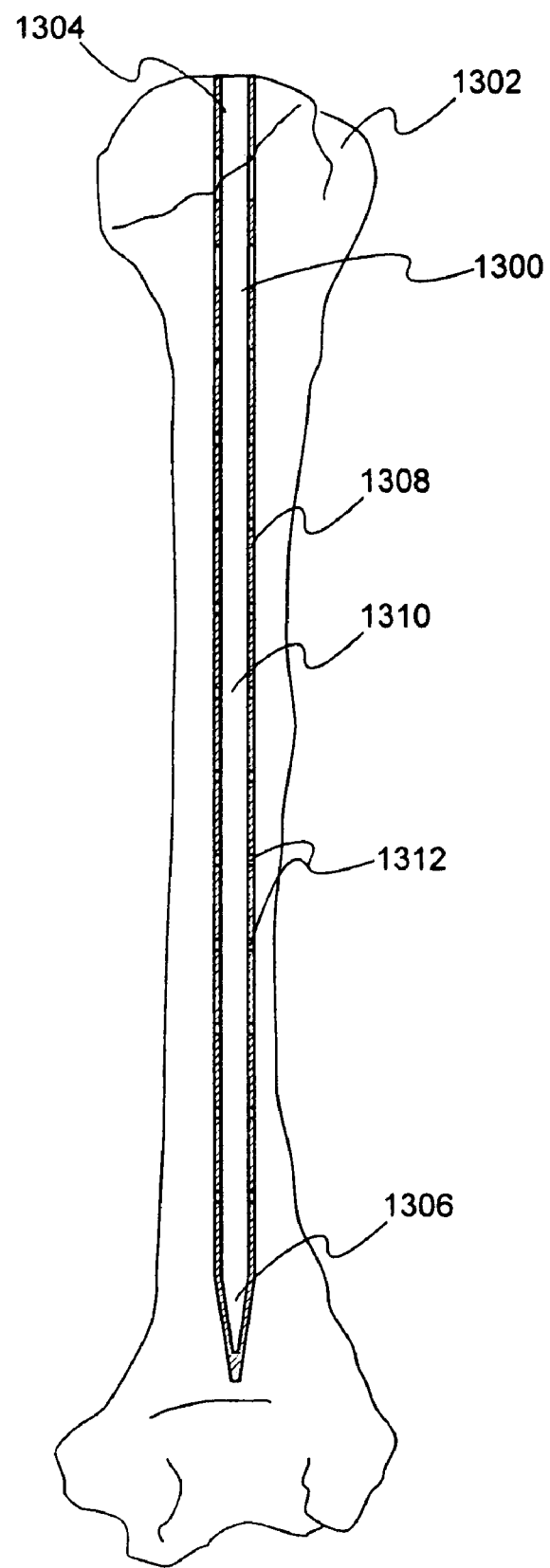
FIG. 14 shows a cross-sectional view of the fixation nail of FIG. 13.
Figure 15:
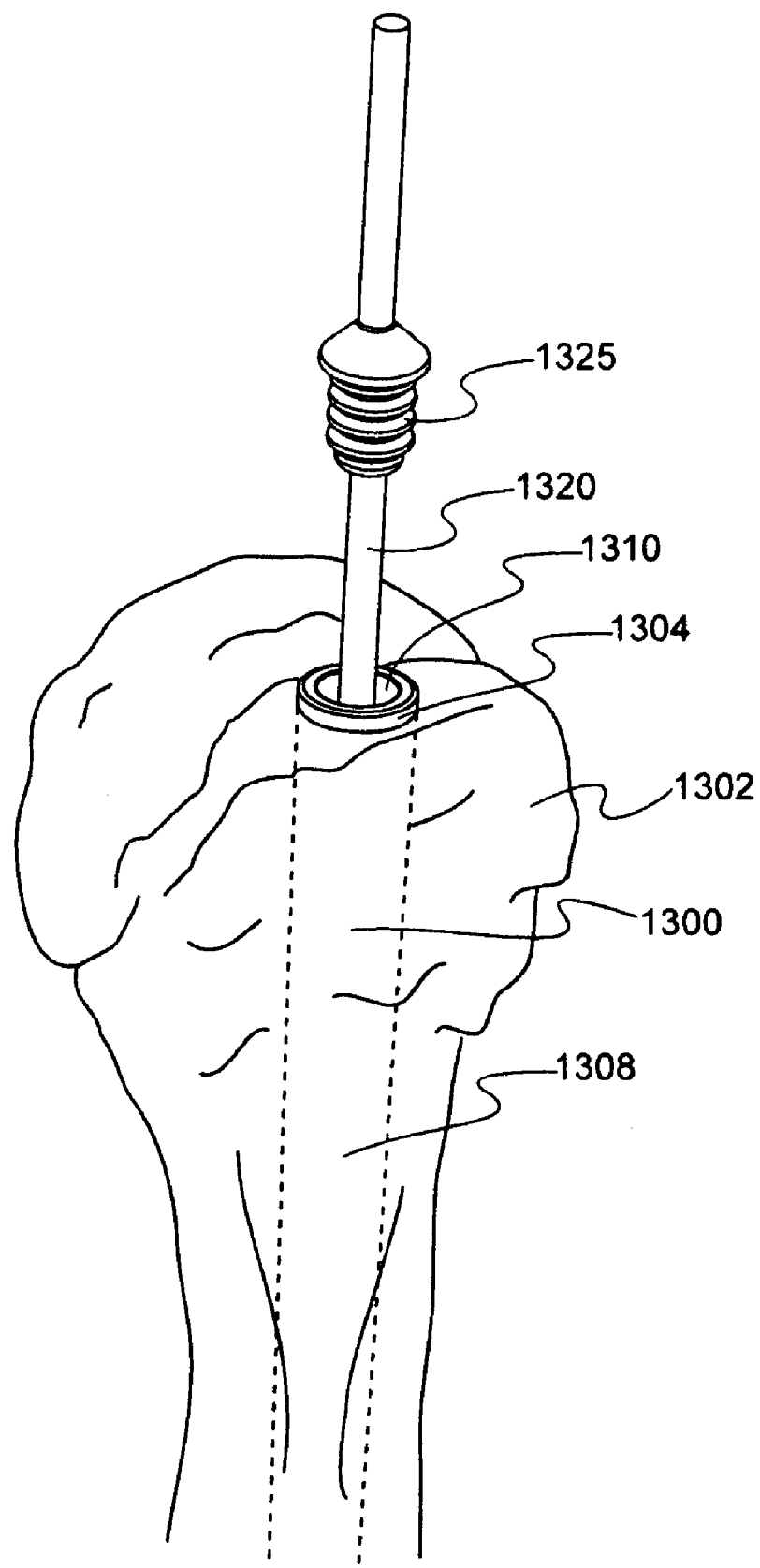
FIG. 15 shows a perspective view of a bone-screw insert being inserted into the fixation nail of FIG. 13.

Referring now to FIG. 13, there is disclosed a humerus fixation nail 1300 disposed within a humerus 1302. The fixation nail has two ends 1304 and 1306 connected by a shaft 1308. The fixation nail includes a cannulated portion 1310, which is best seen in the cross-sectional view of FIG. 14, and fixation nail fenestrations 1312 along the length of the cannulated portion 1310. One end of the cannulated portion 1310 of the fixation nail 1300 maybe configured to accept a nail insert 1320. This is demonstrated in FIG. 15 which shows a perspective view of a nail insert 1320 being inserted into the cannulated portion 1310 of the fixation nail 1300. The fixation nail 1300 has internal threads (not shown) on one end of its cannulated portion 1310 to promote fixation of the nail insert 1320 which also has threads 1325 on one end.

Figure 16:
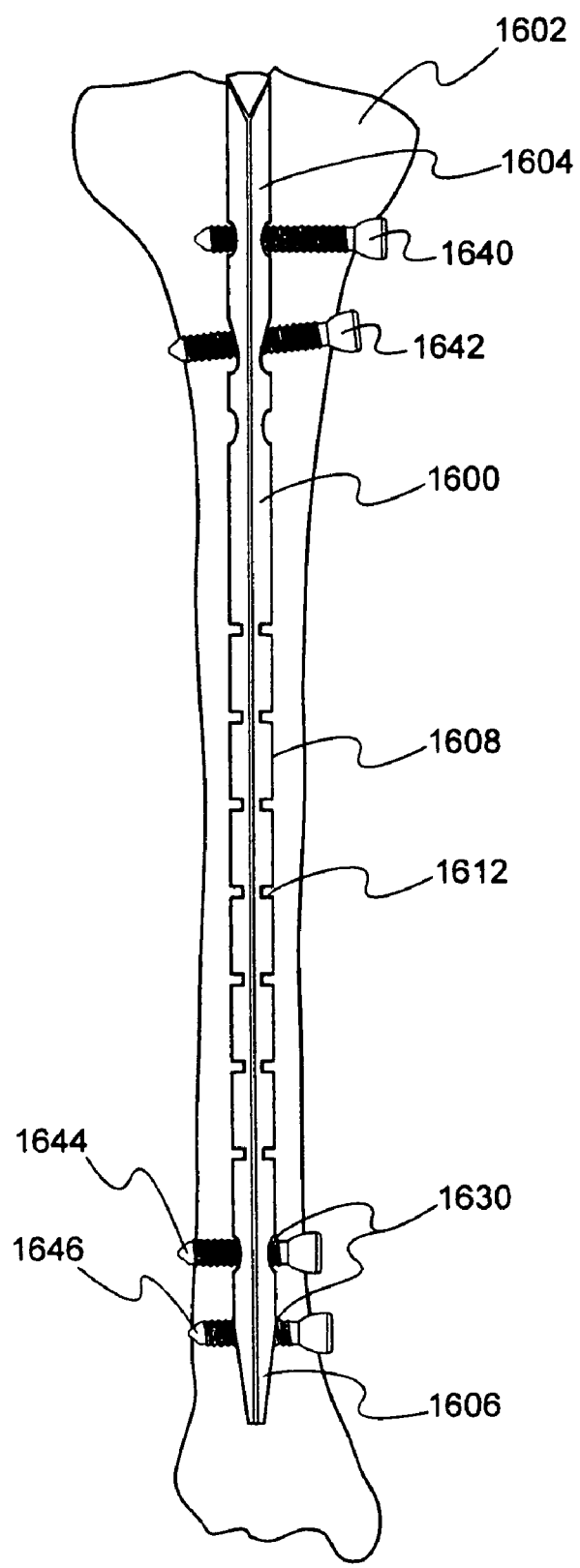
FIG. 16 shows a fixation nail inserted into the tibia bone of a patient.
Figure 17:
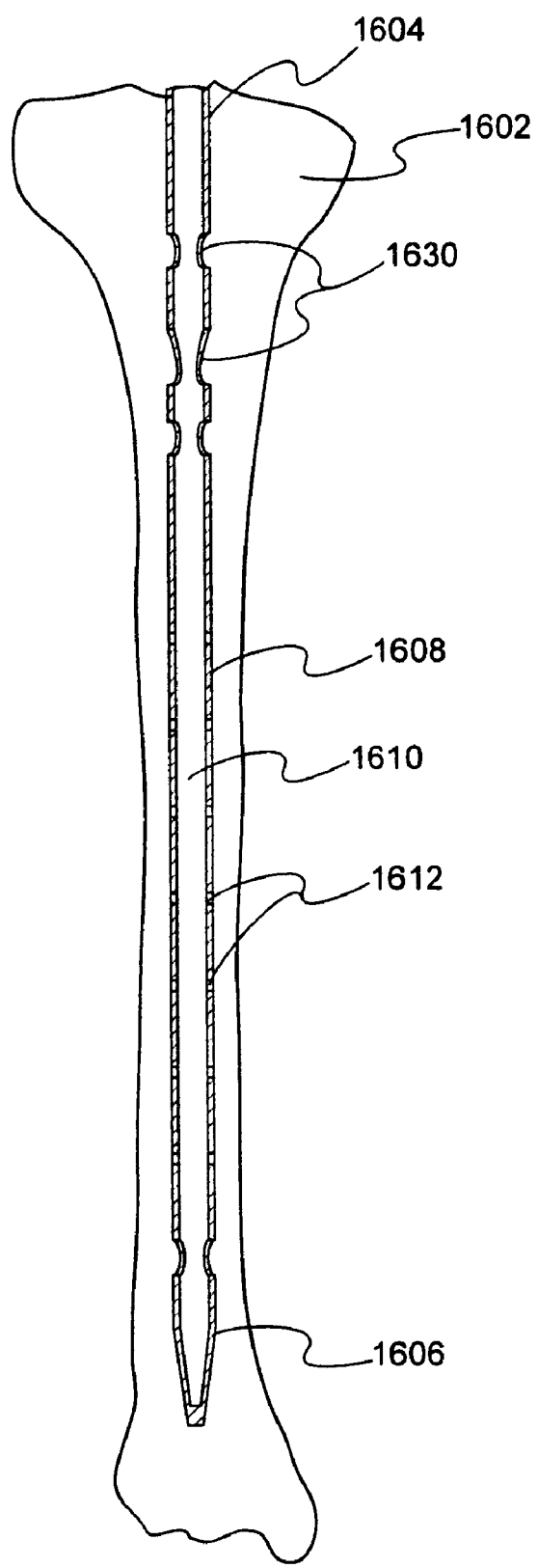
FIG. 17 shows a cross-sectional view of the fixation nail of FIG. 16.
Figure 18:
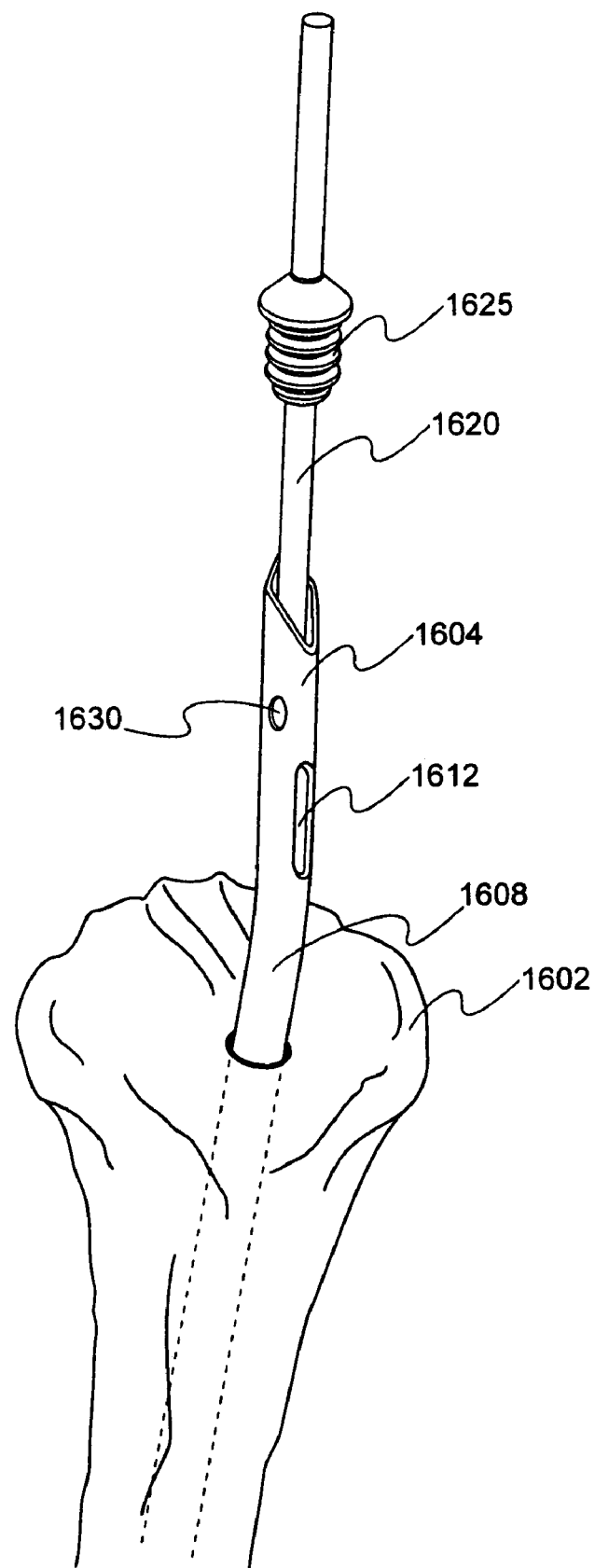
FIG. 18 shows a perspective view of the fixation nail of FIG. 16.

Referring now to FIG. 16, there is disclosed a tibia fixation nail 1600 disposed within a tibia 1602. The fixation nail has two ends 1604 and 1606 connected by a shaft 1608. The fixation nail includes a cannulated portion 1610, which is best seen in the cross-sectional view of FIG. 17, and fixation nail fenestrations 1612 along the length of the cannulated portion 1610. One end of the cannulated portion 1610 of the fixation nail 1600 may be configured to accept a nail insert. This is demonstrated in FIG. 18 which shows a perspective view of the a nail insert 1620 being inserted into the cannulated portion 1610 of the fixation nail 1600. The fixation nail 1600 has internal threads (not shown) on one end of its cannulated portion 1610 to promote fixation of the nail insert 1620 which also has threads 1625 on one end. As shown in the figures, the fixation nail need not be straight along its entire length, but may include one or more angles to facilitate the placement of the nail into a bone. The fixation nail may define one or more bores 1630 through its length through which fixation screws 1640, 1642, 1644 and 1646 may be passed in order to affix the fixation nail to the bone. The fixation screws may pass through the fixation nail substantially perpendicular to the long axis of the nail or they may pass through the nail at acute or obtuse angles with respect to the long axis of the nail. The bores may be aligned substantially parallel with respect to one another, substantially perpendicular with respect to one another or may be aligned at angles between parallel and perpendicular.

Figure 19:
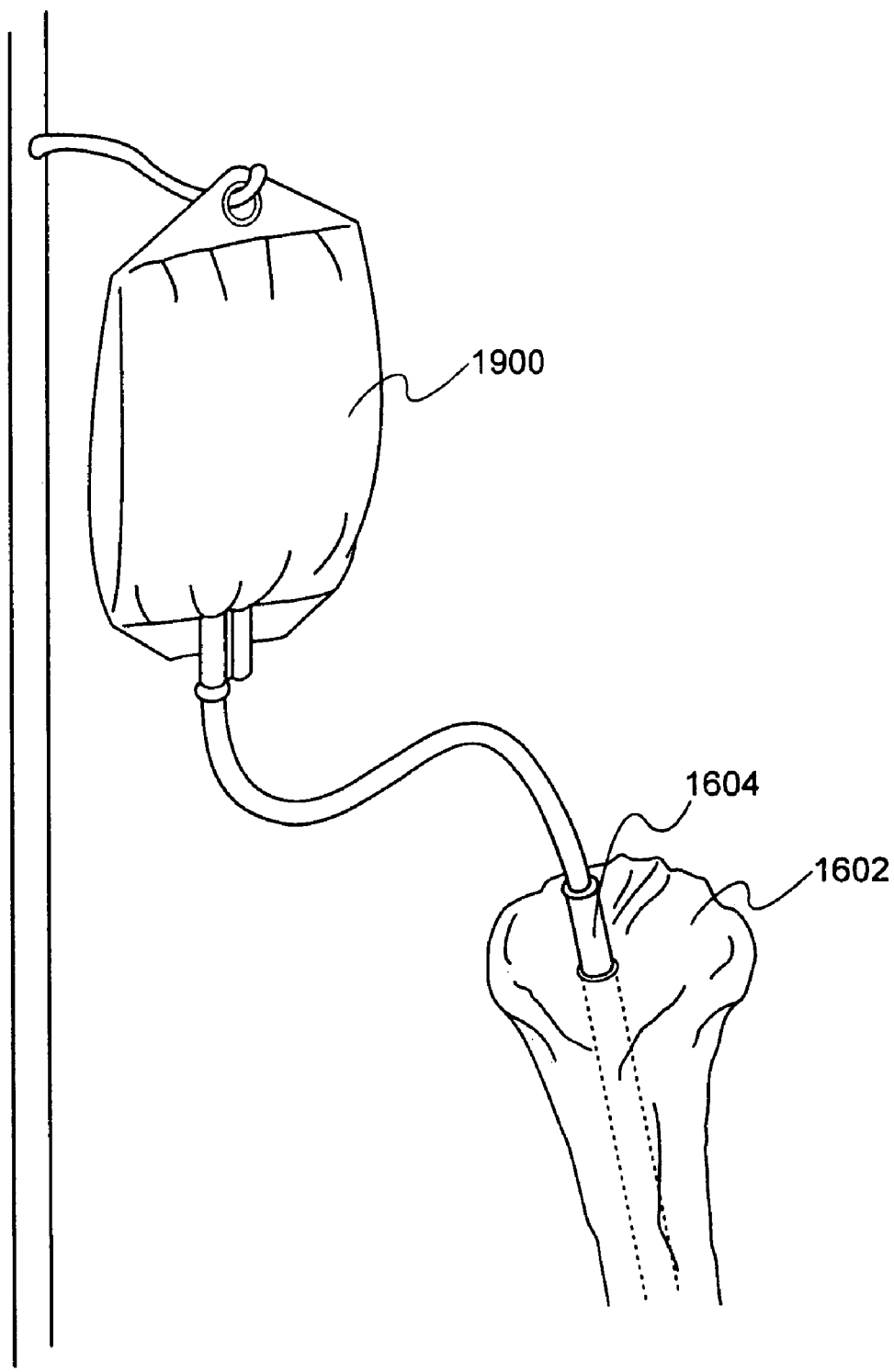
FIG. 19 shows a perspective view of an IV being used to provide a liquid to the fixation nail of FIG. 16.
Figure 20:
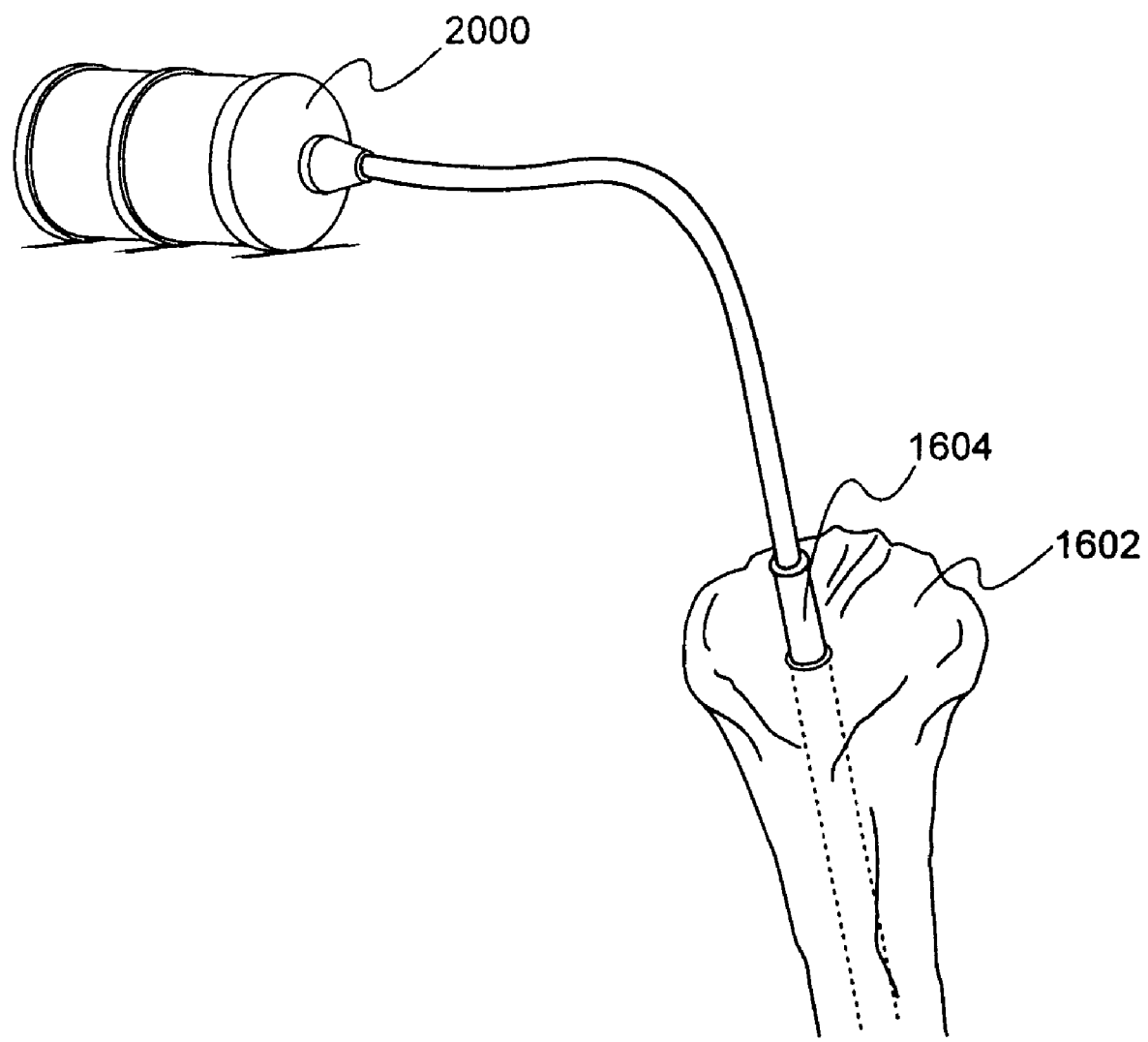
FIG. 20 shows a perspective view of a pump assembly being used to provide a liquid to the fixation nail of FIG. 16.

As discussed above, in certain applications it may be desirable that the substance to be delivered to the bone be stored in a reservoir prior to delivery. FIG. 19 discloses one illustrative embodiment of the invention in which an IV 1900 serves as a reservoir for delivering a substance to a tibia via the fixation nail of FIG. 18. FIG. 20 discloses an alternative embodiment where a pump 2000 serves as the reservoir for delivering a substance to a tibia via the fixation nail of FIG. 18.

In one embodiment of the invention, the delivery pathway between one or more insert fenestrations and one or more bone screw fenestrations is defined by two balloons, each of which is inflated between the outside of the insert and the inside of the bone screw to form a seal between the insert and the bone screw. This embodiment is exemplified in FIGS. 21 and 22. FIG. 21 shows a bone screw insert 2100 having a fenestration 2110 along its length. A first balloon 2120 is disposed around the outside of the insert 2100 above the fenestration 2110 and a second balloon 2130 is disposed around the outside of the insert 2100 below the fenestration 2110. The insert optionally has threads 2140 at one end that interlock with bone screw threads 2150 in a bone screw 2160 to help fix the insert 2100 into the bone screw 2160. The first and second balloons may be inserted into a bone screw in a deflated state. As shown in FIG. 22, when the insert is in place inside the bone screw the balloons 2120 and 2130 are disposed above and below one or more fenestrations 2170 in the bone screw. Once the insert is in place, the balloons may be inflated to form a seal between the outside 2180 of the insert 2100 and the inside 2190 of the bone screw 2160, isolating the insert fenestration 2110 and the bone screw fenestrations 2170 between the balloons. In this manner, the balloons help to define a delivery pathway between one or more insert fenestrations and one or more bone screw fenestrations.

Figure 23:
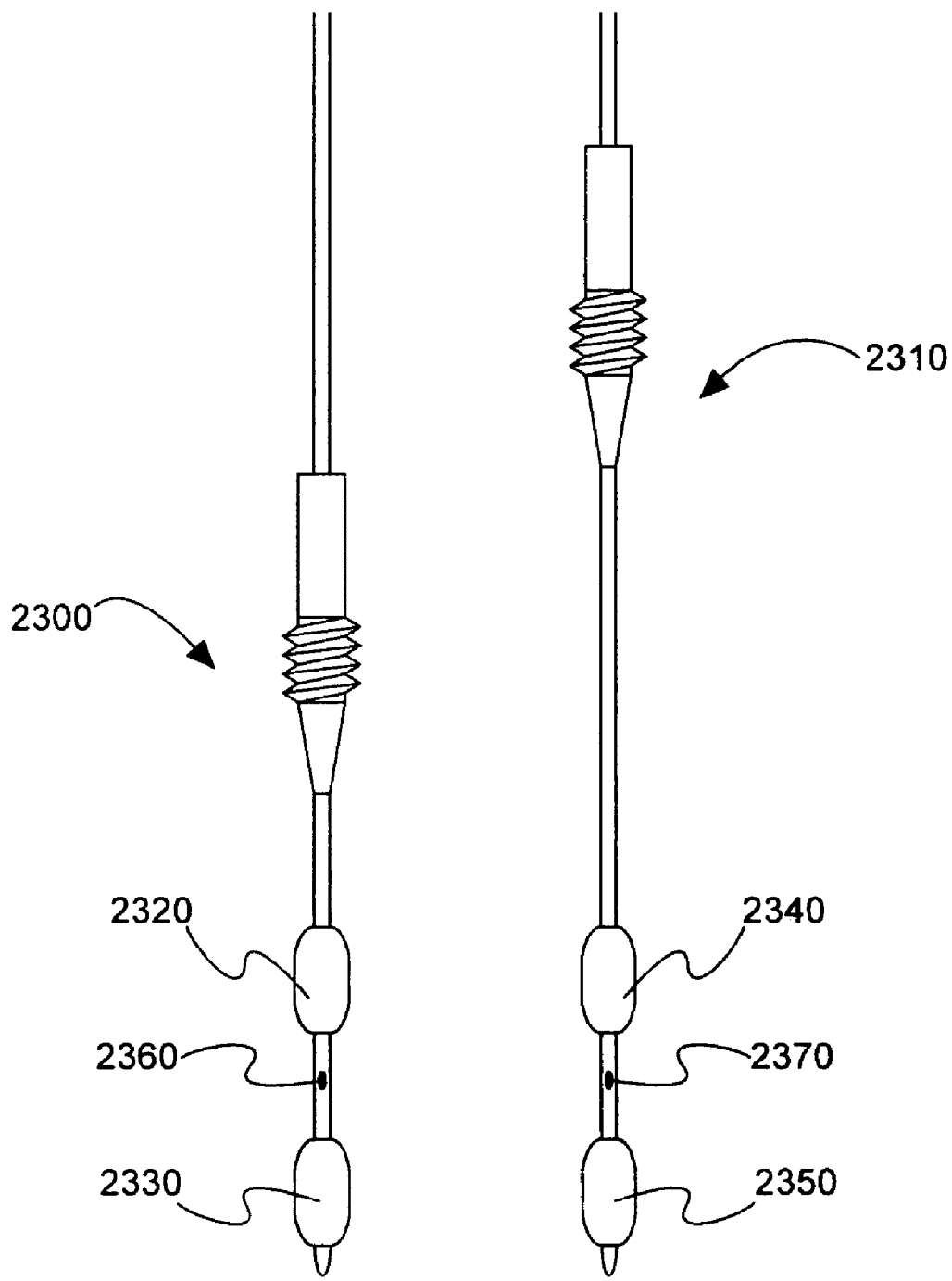
FIG. 23 shows two inserts of different lengths having balloons disposed around their shafts.

FIG. 23 shows two different bone-screw inserts 2300 and 2310, each having a pair of balloons 2320, 2330 and 2340, 2350 disposed along its length and situated above and below an insert fenestration 2360 and 2370. The bone-screw inserts have different lengths, such that they may be adapted for insertion into bone screws of different lengths or may be used to isolate fenestrations at different locations along the shaft of a given bone screw. Although the insert and bone screw fenestrations of FIGS. 21-23 are isolated between two inflated balloons, it should be understood that other configurations are possible. For example, one or more insert fenestrations and one or more bone screw fenestrations could be isolated between a single inflated balloon and the top end or the bottom end of the bone screw.

Another aspect of the present invention is a method of administering a substance to a bone. The method comprises introducing a cannulated, fenestrated bone screw into a bone, introducing a cannulated insert into the bone screw, and introducing a substance to be delivered into the cannulated portion of the insert. Under some circumstances, one may find it advantageous to introduce the insert into the bone screw, in its entirety or only partially, prior to introducing the bone screw into the bone. This sequence might be preferred in order to shorten the overall surgery time, or to reduce the amount of material that enters the bone-screw fenestrations from outside the screw during screw insertion, for example. Alternately, other circumstances may make it more advantageous to introduce the insert into the bone screw, in its entirety or only partially, after the bone screw is introduced into the bone. This latter sequence might be preferred in order to be able to determine which screw fenestrations are located at the optimum location for delivery of the desired substance, and thus what insert configuration or length should be used to facilitate substance delivery to those bone-screw fenestrations and not others. Other sequences can be envisioned by one skilled in the art, such as for example, partially introducing the bone screw into a bone, partially or completely inserting the insert into the bone screw, and then completing the insertion of the bone screw into the bone. Even more sequence variations are possible when one considers the additional step of introducing the substance into the cannulated portion of the bone screw insert, and all such sequence variations are to be included within the scope of this disclosure.

In practicing the current invention it may also be found advantageous to drill a pilot hole in the one or more bones or bone pieces in order to facilitate introduction of the bone screw. In this regard it may be found advantageous to use bone screws with self-tapping threads, or to pre-cut the threads in the bone prior to bone screw insertion.

When the bone screw is a fixation screw, the present invention may further comprise the method of holding or fixing two or more bones or bone pieces in a fixed spatial relationship with respect to each other. Such a method may be desirable when it is desired to deliver a substance such as a medicant or therapeutic to the vicinity of a site where a peripheral skeletal fracture or an osteotomy is mended, a spondyloysis or an odontoid fracture repaired, or lumbar facet joints are fused.

The present invention may further comprise the method of delivering a substance to the vicinity of a bone including the steps of attaching a reservoir, a pump, or both, to the bone screws or bone-screw inserts disclosed herein. Such reservoirs and pumps may aid in the continuous, regulated, or long-term delivery of the desired substance to the vicinity of a bone, thereby facilitating the healing process or the overall health of the bone and its surrounding tissues.

What is claimed is:

1. A method of administering a substance to a bone, the method comprising:
    (a) introducing a bone screw into a bone, the bone screw comprising two ends connected by a shaft, wherein the shaft is cannulated along at least a portion of its length, and further wherein the bone screw comprises one or more bone screw fenestrations disposed along the cannulated portion of the bone screw shaft;
    (b) introducing an insert into the cannulated portion of the bone screw shaft, the insert comprising two ends connected by a shaft, wherein the insert is cannulated along at least a portion of its length, wherein the insert further comprises at least one balloon disposed around a portion of its length, and further wherein the insert comprises one or more insert fenestrations along the cannulated portion of the insert between the two ends of the insert;
    (c) introducing a substance into the cannulated portion of the insert;
    (d) placing the insert into a first position wherein none of the one or more insert fenestrations align with the one or more bone screw fenestrations such that the substance is maintained within the cannulated portion of the insert;
    (e) placing the insert into a second position wherein the substance is allowed to flow from the cannulated portion of the insert through at least one of the bone screw fenestrations to the bone; and
    (f) inflating the balloon in the cannulated portion of the bone screw shaft to form a seal between the insert and the bone screw.

2. The method of claim 1 wherein at least part of the insert is introduced into the bone screw prior to introducing the bone screw into the bone.

3. The method of claim 1 wherein at least part of the insert is introduced into the bone screw after introducing the bone screw into the bone.

4. The method of claim 1 wherein the bone screw is a fixation screw.

5. The method of claim 1 wherein the bone screw is a fixation nail.

6. The method of claim 1 wherein a peripheral skeletal fracture is mended, an osteotomy is mended, a spondyloysis is repaired, an odontoid fracture repaired, or lumbar facet joints are fused by the insertion of the bone screw into the bone.

7. The method of claim 1 further comprising attaching a reservoir to at least one end of the bone screw or insert.

8. The method of claim 1 further comprising attaching a pump to at least one end of the bone screw or insert.

9. The method of claim 7 wherein the reservoir is implanted subcutaneously.

10. The method of claim 8 wherein the pump is implanted subcutaneously.

11. A method of administering a substance to a bone, the method comprising:
   (a) introducing a bone screw into a bone, the bone screw comprising two ends connected by a shaft, wherein the shaft is cannulated along at least a portion of its length, and further wherein the bone screw comprises one or more bone screw fenestrations disposed along the cannulated portion of the bone screw shaft;
   (b) introducing an insert into the cannulated portion of the bone screw shaft, wherein the insert is cannulated along at least a portion of its length, wherein the insert further comprises at least one balloon disposed around a portion of its length, and further wherein the insert is permeable to the substance to be administered;
   (c) introducing a substance into the cannulated portion of the insert;
   (d) placing the insert into a first position wherein the insert prevents at least some material from entering the cannulated portion of the bone screw through all of the one or more bone screw fenestrations;
   (e) placing the insert into a second position wherein the substance is allowed to pass from the cannulated portion of the insert through at least one of the bone screw fenestrations to the bone; and
   (f) inflating the balloon in the cannulated portion of the bone screw shaft to form a seal between the insert and the bone screw.

\* \* \* \* \*

UNITED STATES PATENT AND TRADEMARK OFFICE
CERTIFICATE OF CORRECTION

PATENT NO.        : 7,608,062 B2                                              Page 1 of 1
APPLICATION NO.   : 10/682307
DATED             : October 27, 2009
INVENTOR(S)       : Patrick J. Sweeney It is certified that error appears in the above-identified patent and that said Letters Patent is hereby corrected as shown below:

On the Title page,

[*] Notice:   Subject to any disclaimer, the term of this patent is extended or adjusted under
              35 U.S.C. 154(b) by 576 days.

Delete the phrase "by 576 days" and insert -- by 950 days --

Signed and Sealed this

Twenty-fourth Day of August, 2010

David J. Kappos
*Director of the United States Patent and Trademark Office*